United States Patent
Im et al.

(10) Patent No.: US 9,833,413 B2
(45) Date of Patent: Dec. 5, 2017

(54) PHARMACEUTICAL COMBINATION FORMULATION COMPRISING AMLODIPINE, LOSARTAN AND ROSUVASTATIN

(71) Applicant: HANMI PHARM. CO., LTD., Hwaseong-si, Gyeonggi-do (KR)

(72) Inventors: Ho Taek Im, Yongin-si (KR); Myoung Ki Jeong, Suwon-si (KR); Yong Il Kim, Suwon-si (KR); Jae Hyun Park, Suwon-si (KR); Jong Soo Woo, Suwon-si (KR); Hyuk Jun Cho, Suwon-si (KR)

(73) Assignee: HANMI PHARM. CO., LTD, Hwaseong-si (KR)

( * ) Notice: Subject to any disclaimer, the term of this patent is extended or adjusted under 35 U.S.C. 154(b) by 0 days.

(21) Appl. No.: 15/039,238

(22) PCT Filed: Nov. 20, 2014

(86) PCT No.: PCT/KR2014/011205
§ 371 (c)(1),
(2) Date: May 25, 2016

(87) PCT Pub. No.: WO2015/080433
PCT Pub. Date: Jun. 4, 2015

(65) Prior Publication Data
US 2017/0027871 A1 Feb. 2, 2017

(30) Foreign Application Priority Data
Nov. 29, 2013 (KR) .................. 10-2013-0147883

(51) Int. Cl.
*A61K 9/24* (2006.01)
*A61K 31/505* (2006.01)
*A61K 31/4422* (2006.01)
*A61K 31/4178* (2006.01)
*A61K 9/20* (2006.01)

(52) U.S. Cl.
CPC .......... *A61K 9/209* (2013.01); *A61K 31/4178* (2013.01); *A61K 31/4422* (2013.01); *A61K 31/505* (2013.01); *A61K 9/2018* (2013.01); *A61K 9/2054* (2013.01); *A61K 9/2095* (2013.01)

(58) Field of Classification Search
None
See application file for complete search history.

(56) References Cited

U.S. PATENT DOCUMENTS

| | | | |
|---|---|---|---|
| 8,673,944 B2* | 3/2014 | Park ................. | A61K 9/2013 424/465 |
| 9,161,933 B2* | 10/2015 | Park ................. | A61K 9/2013 |
| 2006/0110450 A1* | 5/2006 | Eisenreich ........ | A61K 31/455 424/464 |
| 2009/0093542 A1* | 4/2009 | Cooper ............. | A61K 31/131 514/551 |
| 2010/0233261 A1* | 9/2010 | Woo ................. | A61K 31/4178 424/475 |

FOREIGN PATENT DOCUMENTS

| | | |
|---|---|---|
| CN | 101690816 A | 4/2010 |
| EP | 1 314 425 A1 | 5/2003 |
| WO | 2009/154810 A2 | 12/2009 |
| WO | 2013/100630 A1 | 7/2013 |
| WO | 2013/154390 A1 | 10/2013 |

OTHER PUBLICATIONS

Mitesh R. Bhoot Rama, "Formulation and Evaluation of Bilayer Tablets of Two Incompatible Drugs Amlodipine Besilate and Losartan Potassium", Int. Res. J. Pharm., Sep. 2013, pp. 136-142, vol. 4, No. 9.
International Searching Authority International Search Report for PCT/KR2014/011205 dated Feb. 27, 2015.
International Searching Authority Written Opinion for PCT/KR2014/011205 dated Feb. 27, 2015.
European Patent Office, Communication dated May 2, 2017 issued in counterpart European Application No. 14866739.7.

* cited by examiner

*Primary Examiner* — Richard Schnizer
*Assistant Examiner* — Katherine Peebles
(74) *Attorney, Agent, or Firm* — Sughrue Mion, PLLC

(57) ABSTRACT

Disclosed is a pharmaceutical combination formulation comprising a first discrete part containing amlodipine and rosuvastatin and a second discrete part containing losartan, which exhibits improved dissolution rate and stability. The inventive combination formulation comprising amlodipine, losartan and rosuvastatin having different action mechanisms from one another can be effectively used to prevent or treat a cardiovascular disorder. Designed to minimize an interaction among active ingredients, the pharmaceutical combination formulation exhibits excellent storage stability and dissolution rates of amlodipine, losartan and rosuvastatin, and thus can be useful in pharmaceutical industries.

10 Claims, 16 Drawing Sheets

PHARMACEUTICAL COMBINATION FORMULATION COMPRISING AMLODIPINE, LOSARTAN AND ROSUVASTATIN

CROSS REFERENCE TO RELATED APPLICATIONS

This application is a National Stage of International Application No. PCT/KR2014/011205 filed Nov. 20, 2014, claiming priority based on Korean Patent Application No. 10-2013-0147883 filed Nov. 29, 2013, the contents of all of which are incorporated herein by reference in their entirety.

FIELD OF THE INVENTION

The present invention relates to a pharmaceutical combination formulation comprising amlodipine, losartan and rosuvastatin. More specifically, it relates to a pharmaceutical combination formulation comprising a first discrete part containing amlodipine and rosuvastatin and a second discrete part containing losartan, which exhibits improved dissolution rate and stability.

BACKGROUND OF THE INVENTION

About 90 to 95% of hypertension cases are categorized as primary hypertension which means high blood pressure with no obvious underlying medical cause. The exact cause of primary hypertension is unknown, but a number of factors including increase in cardiac output (the volume of blood being pumped out by the heart) or peripheral resistance are believed to contribute to the onset of the disease. Risk factors that are related to hypertension include psychological and environmental factors such as drinking, smoking, aging, lack of exercise, obesity, too much salt in the diet, stress and the like. Genetically, when both parents have hypertension, the offspring has an 80% chance of having hypertension; if one of the parents has hypertension, the offspring has a 25 to 50% chance of having hypertension.

The ultimate goal in the treatment of hypertension is to maintain an optimal blood pressure to minimize tissue damage caused by hypertension. Thus, adopting a preventative lifestyle is as important as taking a medication. It is a goal to keep blood pressure less than 140/90 mmHg for patients with hypertension, and less than 130/80 mmHg for hypertensive patients with diabetic or nephritis complications.

If hypertension is treated, it may reduce mortality caused by stroke and cardiovascular disorders. When patients with hypertension are properly treated, it is estimated that risks of experiencing stroke, myocardial infarction and heart failure are lowered by about 35~40%, 20~25% and more than 50%, respectively. Lowering systolic blood pressure by 5 mmHg reduces all-cause mortality by 7% on a population basis, while mortality for coronary heart disease and stroke can be reduced by 9% and 14%, respectively. Also, blood pressure is closely related to Alzheimer's disease and, thus, blood pressure management may reduce the risk of Alzheimer's disease.

Since avoiding risk factors for cardiovascular complications is very important to hypertensive patients as explained above, continuous blood pressure management is critical to those patients. Moreover, since it is required to take medications for a long period of time in the treatment of hypertension, a combination of drugs of different mechanisms has an advantage over individual drugs in terms of preventive and therapeutic effect. Also, a combination therapy reduces doses of individual drugs, thereby reducing side effects which may occur due to long-term administration of individual drugs.

In general, medications that are often used in the treatment of hypertension are categorized into, according to their mechanism of action, diuretics, sympatholytic agents and vasodilators; and vasodilators are further categorized in accordance with their mechanism of action, as follows: angiotensin-converting enzyme (ACE) inhibitors, angiotensin II receptor blockers and calcium channel blockers.

Meanwhile, hyperlipidemia is a disorder in which an excessively high level of lipids in the blood cause a buildup of plaque on the walls of the arteries, followed by inflammation and, ultimately, cardiovascular disorders. In recent years, an abnormal amount of lipids in the blood is defined as dyslipidemia.

In the treatment of hyperlipidemia, non-drug therapies such as lifestyle changes (including physical exercise and diets) and maintaining ideal body weight, may be used in conjunction with medication. Statin-based drugs are often used, and these drugs act as an HMG-CoA reductase inhibitor which has an ability to inhibit cholesterol synthesis and thereby to cause significant reduction in plasma LDL-cholesterol levels, and also result in partial reduction in triglycerides levels.

Amlodipine is a generic name for 3-ethyl-5-methyl-2-(2-aminoethoxy-methyl)-4-(2-chlorophenyl)-6-methyl-1,4-dihydro-3,5-pyridine dicarboxylate, and, in particular, amlodipine besylate is commercially available under the trade name Novasc®. Amlodipine camsylate, as disclosed in Korean Patent No. 452491, shows superior solubility and stability to amlodipine besylate, and is currently available under the trade name Amodipin®. Amlodipine blocks calcium channel, and is useful in the treatment of cardiovascular disorders such as angina, hypertension and congestive heart failure.

Losartan is a generic name for 2-butyl-4-chloro-1-[2'-(1H-tetrazol-5-yl)[1,1'-biphenyl]-4-yl]methyl]-1H-imidazol-5-methanol, as disclosed in U.S. Pat. Nos. 5,608,075, 5,138,069 and 5,153,197. Currently losartan potassium is commercially available under the trade name Cozaar®. By blocking the interaction of angiotensin II and its receptor, losartan is mainly used for treating hypertension, heart failure, ischemic peripheral circulatory disorder, myocardial ischemia (angina pectoris), diabetic neuropathy and glaucoma, and also for preventing the progression of post-myocardial infarction heart failure.

A combination formulation of amlodipine and losartan that have different mechanism of action from each other has an advantage over the individual drugs in terms of preventive and therapeutic effect. In addition, such formulation reduces doses of the individual drugs, thereby decreasing side effects which may occur due to a long-term administration of the individual drugs. The combination formulation is disclosed in Korean Patent Nos. 1160151, 1232296, etc., and currently sold under the trade name Amosartan®.

Rosuvastatin is a generic name for (E)-7-[4-(4-fluorophenyl)-6-isopropyl-2-[methyl(methylsulfonyl)amino]pyrimidin-5-yl]-(3R,5S)-3,5-dihydroxyhep-6-enoic acid, and currently available under the trade name Crestor®. Such statin-based drugs act as an HMG-CoA reductase inhibitor which inhibits cholesterol synthesis and reduces plasma LDL-cholesterol and triglycerides concentrations. Rosuvastatin is very effective in the treatment of hypercholesterolemia, hyperlipoproteinemia or atherosclerosis.

The co-occurrence rate of hypertension and hyperlipidemia is approximately 49%, and co-administration of Amosartan® and statin-based drugs takes up about 30% in the drug treatment of cardiovascular disorders.

In clinical research, there is a growing need for a combination formulation including amlodipine, losartan and rosuvastatin having different mechanisms for more effective treatment of cardiovascular disorders. However, it is difficult to commercialize such formulation due to complexity in designing and a possibility of deterioration in dissolution and stability due to interaction among the active ingredients.

Leading to the present invention, the present inventors have conducted intensive research to redress the problems of the conventional formulations, and found that dissolution rate and stability of the active ingredients varied depending on the structure of a bilayer tablet and the manufacturing method thereof, and thus accomplished a pharmaceutical combination formulation comprising amlodipine, losartan and rosuvastatin having improved dissolution rate and stability.

SUMMARY OF THE INVENTION

Therefore, it is an object of the present invention to provide a pharmaceutical combination formulation for the treatment of a cardiovascular disorder comprising amlodipine, losartan and rosuvastatin, having different action mechanisms from one another, which exhibits excellent dissolution and stability properties.

In accordance with one aspect of the present invention, there is provided a pharmaceutical combination formulation for the prevention or treatment of a cardiovascular disorder, comprising: (1) a first discrete part comprising amlodipine or a pharmaceutically acceptable salt thereof, rosuvastatin or a pharmaceutically acceptable salt thereof and a pharmaceutically acceptable additive; and (2) a second discrete part comprising losartan or a pharmaceutically acceptable salt thereof and a pharmaceutically acceptable additive, wherein said discrete parts are physically separated from each other.

The pharmaceutical combination formulation comprising amlodipine, losartan and rosuvastatin can be effectively used to prevent or treat a cardiovascular disorder. Designed to minimize an interaction among active ingredients, the pharmaceutical combination formulation exhibits excellent storage stability and dissolution rates of amlodipine, losartan and rosuvastatin, and thus can be useful in pharmaceutical industries.

BRIEF DESCRIPTION OF THE DRAWING

The above and other objects and features of the present invention will be more clearly understood from the following detailed description in conjunction with the accompanying drawings, in which.

DETAILED DESCRIPTION OF THE INVENTION

The present invention provides a pharmaceutical combination formulation for the prevention or treatment of a cardiovascular disorder, comprising: (1) a first discrete part comprising amlodipine or a pharmaceutically acceptable salt thereof, rosuvastatin or a pharmaceutically acceptable salt thereof and a pharmaceutically acceptable additive; and (2) a second discrete part comprising losartan or a pharmaceutically acceptable salt thereof and a pharmaceutically acceptable additive, wherein said discrete parts are physically separated from each other.

The combination formulation according to the present invention comprises the first and the second discrete parts in which said discrete parts are physically separated, i.e., amlodipine and losartan are separately contained. Thus, an interaction between amlodipine and losartan is prevented, thereby exhibiting improved stability.

Figure 1:
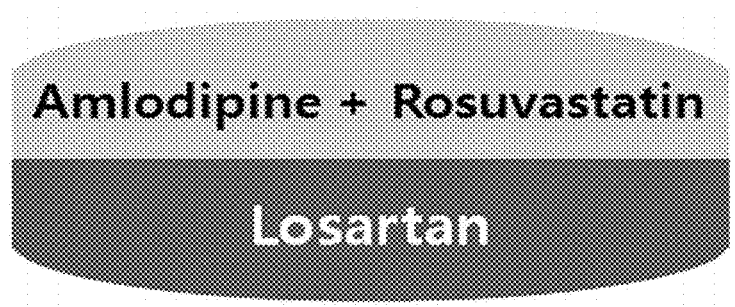
FIG. 1 is a schematic view showing a bilayer tablet according to one embodiment of the present invention.

In one embodiment of the present invention, the first discrete part and the second discrete part in the combination formulation may be a first layer and a second layer, respectively. In other words, the combination formulation may be in the form of a bilayer tablet comprising: (1) a first layer comprising amlodipine or a pharmaceutically acceptable salt thereof, rosuvastatin or a pharmaceutically acceptable salt thereof and a pharmaceutically acceptable additive; and (2) a second layer comprising losartan or a pharmaceutically acceptable salt thereof and a pharmaceutically acceptable additive (see FIG. 1). Besides a bilayer tablet, in another embodiment of the present invention, the combination formulation may be prepared in various forms where a first discrete part and a second discrete part are physically separated from each other (for example, core-shell structure).

The combination formulation of the present invention comprises amlodipine or a pharmaceutically acceptable salt thereof in the first discrete part (or the first layer). The pharmaceutically acceptable salt of amlodipine employed in the present invention may be prepared by using an acid containing a pharmaceutically acceptable anion which can form a non-toxic acid addition salt, e.g., hydrogen chloride, hydrogen bromide, sulfate, phosphate, acetate, malate, fumarate, lactate, tartrate, citrate, gluconate, besylate and camsylate, but are not limited thereto. Preferably, the pharmaceutically acceptable salt of amlodipine is amlodipine besylate and camsylate, more preferably camsylate. Also, amlodipine of the present invention includes a racemic mixture and (S)-amlodipine. Amlodipine or a pharmaceutically acceptable salt thereof may be administered at a daily dose of from 5 to 10 mg.

The combination formulation of the present invention comprises rosuvastatin or a pharmaceutically acceptable salt thereof in the first discrete part (or the first layer). Examples of the pharmaceutically acceptable salt of rosuvastatin include inorganic salts having polycation, preferably rosuvastatin calcium, but are not limited thereto. Rosuvastatin or a pharmaceutically acceptable salt thereof may be administered at a daily dose of from 10 to 20 mg.

The combination formulation of the present invention comprises losartan or a pharmaceutically acceptable salt thereof in the second discrete part (or the second layer). Examples of the pharmaceutically acceptable salt of losartan include losartan potassium, but are not limited thereto. Losartan or a pharmaceutically acceptable salt thereof may be administered at a daily dose of from 45 to 100 mg.

In the combination formulation of the present invention, amlodipine or a pharmaceutically acceptable salt thereof, rosuvastatin or a pharmaceutically acceptable salt thereof and losartan or a pharmaceutically acceptable salt thereof may be admixed in a weight ratio of 1:1~4:10~20, but not limited thereto.

In the present invention, the first discrete part (or the first layer) and the second discrete part (or the second layer) of the combination formulation may further comprise a pharmaceutically acceptable additive, e.g., a pharmaceutically acceptable carrier or excipient. Examples of the pharmaceutically acceptable carrier or excipient include lactose (lactose hydrate), micro-crystalline cellulose, mannitol, sodium citrate, calcium citrate, calcium phosphate, glycine and starch, a disintegrant (e.g., crospovidone, copovidone, sodium starch glycolate, croscarmellose sodium, and combination silicates) and a binder (e.g., polyvinylpyrrolidone, hydroxypropyl methyl cellulose (HPMC), hydroxypropyl cellulose (HPC), sucrose, gelatin and acacia gum.

In one embodiment, the combination formulation of the present invention comprises lactose hydrate and micro-crystalline cellulose in the first discrete part (or the first layer) as additives. The lactose hydrate may be comprised in an amount of from 20 to 40 wt % based on the total weight of the first discrete part (or the first layer). The micro-crystalline cellulose may be comprised in an amount of from 50 to 70 wt % based on the total weight of the first discrete part (or the first layer). In another embodiment, the lactose hydrate and micro-crystalline cellulose may be employed in a ratio of 1:1.5 to 1:3.

When the lactose hydrate is employed in said range, the lactose hydrate may form hydrophilic channels which promote dissolution of active ingredients, thereby allowing a fast dissolution. A fast dissolution profile cannot be obtained if the amount falls below said range, and if the amount exceeds said range, time required for complete dissolution of the lactose hydrate is extended and thereby slowing down the dissolution of active ingredients. In case of micro-crystalline cellulose, the tableting process becomes easy if the micro-crystalline cellulose is employed in said range. However, an amount smaller than said range may cause some difficulties during the tableting process, whereas an excessive amount may lead to an excessively large size of formulation.

Accordingly, dissolution rates of amlodipine, rosuvastatin and losartan may be improved significantly by employing the lactose hydrate and micro-crystalline cellulose in said range.

In one embodiment, the second discrete part (or the second layer) of the inventive combination formulation may be prepared in a conventional manner, e.g., compaction granulation followed by tableting. In another embodiment, the second discrete part is in the form of granules prepared by a dry roller compaction process. According to the experimental results of the present invention, a combination formulation exhibited improved dissolution rate of amlodipine, rosuvastatin and losartan, as well as excellent dissolution profiles of amlodipine and rosuvastatin when the combination formulation was prepared by tableting a simply mixed first discrete part and a second discrete part prepared by compaction granulation.

A problem of gelation of losartan occurs when a combination formulation is prepared by simply mixing amlodipine, rosuvastatin and losartan. Losartan readily dissolves in purified water and is easily released at a relatively high pH (e.g., pH 4.0, pH 6.8), but is released very slowly at a low pH (e.g., pH 1.2, pH 2.0) because of the gelation. This problem significantly imparts undesired effects on the dissolution rate and bioavailability of formulation because the formulation is first exposed to the acidic gastric juice having a low pH value when orally administered. As the gelation of losartan progresses in the formulation, amlodipine and rosuvastatin are trapped within the losartan gel and dissolve poorly, which is demonstrated in Comparative Example 1. The dissolution result of a single layer tablet of Comparative Example 1 prepared by simply mixing said three ingredients was significantly lower than "80% dissolution at the time of 30 minutes in pH 1.2."

In comparison, the combination formulation of the present invention separates the first discrete part comprising amlodipine and rosuvastatin from the second discrete part comprising losartan, thereby reducing the contact area of losartan. As a result, the gelation of losartan can be prevented under a low pH condition and thus exhibit improved stability and dissolution rate of amlodipine, rosuvastatin and losartan.

Meanwhile, the present invention also provides a fixed-dose combination formulation for the prevention or treatment of a cardiovascular disorder, comprising: (1) a first discrete part comprising amlodipine or a pharmaceutically acceptable salt thereof, rosuvastatin or a pharmaceutically acceptable salt thereof and a pharmaceutically acceptable additive; and (2) a second discrete part comprising losartan or a pharmaceutically acceptable salt thereof and a pharmaceutically acceptable additive, wherein said discrete parts are physically separated from each other.

In one embodiment of the fixed-dose combination formulation, the amount of amlodipine or a pharmaceutically acceptable salt thereof, as converted to amlodipine free base form, is 5 to 10 mg. In one embodiment of the fixed-dose combination formulation, the amount of rosuvastatin or a pharmaceutically acceptable salt thereof, as converted to rosuvastatin free acid form, is 10 to 20 mg. Also, in one embodiment of the fixed-dose combination formulation, the amount of losartan or a pharmaceutically acceptable salt thereof, as converted to losartan free base form, is 45 to 100 mg.

Moreover, in accordance with another aspect thereof, the present invention provides a method for preparing a pharmaceutical combination formulation for the prevention or treatment of a cardiovascular disorder, comprising: a) admixing amlodipine or a pharmaceutically acceptable salt thereof, rosuvastatin or a pharmaceutically acceptable salt thereof and a pharmaceutically acceptable additive; b) admixing losartan or a pharmaceutically acceptable salt thereof and a pharmaceutically acceptable additive; and c) loading a discrete part prepared in Step a) and a discrete part prepared in Step b) into a formulation, wherein said discrete parts are physically separated from each other.

In one embodiment, Step b) further comprises a granulizing step, and in Step c) the discrete part obtained in Step a) and the granules obtained in Step b) are tableted to obtain a bilayer tablet.

In the present invention, the cardiovascular disorder is selected from the group consisting of angina pectoris, hypertension, arteriospasm, cardiac arrhythmia, cardiomegaly, cerebral infarction, congestive heart failure and myocardial infarction, but not limited thereto.

Hereinafter, the present invention is described more specifically by following examples. However, these examples are provided only for illustration purposes, and the present invention is not limited thereto.

Examples 1 to 3: Preparation of Combination Bilayer Tablet by Using Compaction Granulation In accordance with the ingredients as described in Table 1 below, amlodipine camsylate, rosuvastatin calcium, lactose hydrate, micro-crystalline cellulose and crospovidone were admixed, sieved through a 30 mesh screen, added with magnesium stearate and finally admixed in a mixer to obtain a discrete part comprising amlodipine and rosuvastatin.

Meanwhile, losartan potassium, micro-crystalline cellulose, hydroxypropyl cellulose and crospovidone were admixed, and sieved through a 30 mesh screen. Then, the sieved powder was pressed using a roller compactor (WP200, Alexanderwerk) at a minimum compaction force of 20 kN with a roll speed of from 2 to 10 rpm to form granules in the form of flakes. Granules thus obtained were pulverized by using a Fitz Mill (BAS 06, Fitzpatrick, USA), sieved through a 20 mesh screen, added with magnesium stearate and finally admixed in a mixer to obtain a discrete part comprising losartan.

Subsequently, the discrete parts were formulated into a combination bilayer tablet comprising the discrete part comprising amlodipine and rosuvastatin (first layer, upper layer) and the discrete part comprising losartan (second layer, lower layer) by using a tablet press (Kilian Synthesis 700, Germany).

TABLE 1

| Component | Ingredient (mg) | Example 1 | Example 2 | Example 3 |
|---|---|---|---|---|
| Discrete part comprising amlodipine + rosuvastatin | Amlodipine camsylate | 7.8 (Amlodipine, 5 mg) | 7.8 | 7.8 |
| | Rosuvastatin calcium | 20.8 (Rosuvastatin, 20 mg) | 20.8 | 20.8 |
| | Lactose hydrate | 52.0 | 52.0 | 104.0 |
| | Micro-crystalline cellulose | 104.0 | 156.0 | 156.0 |
| | Crospovidone | 10.0 | 10.0 | 10.0 |
| | Magnesium stearate | 2.0 | 2.0 | 2.0 |
| Ratio of lactose hydrate in the first layer | | 26% | 21% | 35% |
| Ratio of micro-crystalline cellulose in the first layer | | 53% | 63% | 52% |
| Discrete part comprising losartan | Losartan potassium | 100.0 (Losartan, 91.6 mg) | 100.0 | 100.0 |
| | Micro-crystalline cellulose | 182.0 | 182.0 | 182.0 |
| | Crospovidone | 15.0 | 15.0 | 15.0 |
| | Hydroxypropyl cellulose | 4.0 | 4.0 | 4.0 |
| | Magnesium stearate | 3.0 | 3.0 | 3.0 |

Comparative Example 1: Preparation of Single-Layer Tablet by Using Dry Direct Tableting In accordance with the ingredients as described in Table 2 below, amlodipine camsylate, rosuvastatin calcium, losartan potassium, lactose hydrate, micro-crystalline cellulose and crospovidone and hydroxypropyl cellulose were admixed, sieved through a 30 mesh screen, added with magnesium stearate and finally admixed in a mixer. The mixed powder was formulated to obtain a single-layer tablet.

TABLE 2

| Ingredient | Comparative Example 1 |
|---|---|
| Amlodipine camsylate | 7.8 (Amlodipine, 5 mg) |
| Rosuvastatin calcium | 20.8 (Rosuvastatin, 20 mg) |
| Losartan potassium | 100.0 (Losartan, 91.6 mg) |
| Lactose hydrate | 52.0 |
| Micro-crystalline cellulose | 286.0 |
| Crospovidone | 25.0 |
| Hydroxypropyl cellulose | 4.0 |
| Magnesium stearate | 5.0 |

Comparative Example 2: Preparation of Bilayer Tablet Using Dry Direct Tableting

In accordance with the ingredients as described in Table 3 below, amlodipine camsylate, rosuvastatin calcium, lactose hydrate, micro-crystalline cellulose, and crospovidone were admixed, sieved through a 30 mesh screen, added with magnesium stearate and finally admixed in a mixer to obtain a discrete part comprising amlodipine and rosuvastatin.

Meanwhile, losartan potassium, micro-crystalline cellulose, hydroxypropyl cellulose and crospovidone were admixed, sieved through a 30 mesh screen, added with magnesium stearate and finally admixed in a mixer to obtain a discrete part comprising losartan.

Subsequently, the discrete parts were formulated into a combination bilayer tablet comprising the discrete part comprising amlodipine and rosuvastatin (first layer, upper layer) and the discrete part comprising losartan (second layer, lower layer) by using a tablet press.

TABLE 3

| Component | Ingredient (mg) | Comparative Example 2 |
|---|---|---|
| Discrete part comprising amlodipine + rosuvastatin | Amlodipine camsylate | 7.8 (Amlodipine, 5 mg) |
| | Rosuvastatin calcium | 20.8 (Rosuvastatin, 20 mg) |
| | Lactose hydrate | 52.0 |
| | Micro-crystalline cellulose | 104.0 |
| | Crospovidone | 10.0 |
| | Magnesium stearate | 2.0 |
| Discrete part comprising losartan | Losartan potassium | 100.0 (Losartan, 91.6 mg) |
| | Micro-crystalline cellulose | 182.0 |
| | Crospovidone | 15.0 |
| | Hydroxypropyl cellulose | 4.0 |
| | Magnesium stearate | 3.0 |

Comparative Examples 3 to 5: Preparation of Bilayer Tablet by Using Compaction Granulation The procedure of Example 1 was repeated except for changing the ratio of lactose and cellulose in accordance with the ingredients as described in Table 4 below to obtain a combination bilayer tablet.

TABLE 4

| Component | Ingredient (mg) | Comparative Example 3 | Comparative Example 4 | Comparative Example 5 |
|---|---|---|---|---|
| Discrete part comprising amlodipine + rosuvastatin | Amlodipine camsylate | 7.8 (Amlodipine, 5 mg) | 7.8 | 7.8 |
| | Rosuvastatin calcium | 20.8 (Rosuvastatin, 20 mg) | 20.8 | 20.8 |
| | Lactose hydrate | — | 52.0 | 104.0 |
| | Micro-crystalline cellulose | 104.0 | 52.0 | 52.0 |
| | Crospovidone | 10.0 | 10.0 | 10.0 |
| | Magnesium stearate | 2.0 | 2.0 | 2.0 |
| | Ratio of lactose hydrate in the first layer | 0% | 36% | 53% |
| | Ratio of micro-crystalline cellulose in the first layer | 72% | 36% | 26% |
| Discrete part comprising losartan | Losartan potassium | 100.0 (Losartan, 91.6 mg) | 100.0 | 100.0 |
| | Micro-crystalline cellulose | 182.0 | 182.0 | 182.0 |
| | Crospovidone | 15.0 | 15.0 | 15.0 |
| | Hydroxypropyl cellulose | 4.0 | 4.0 | 4.0 |
| | Magnesium stearate | 3.0 | 3.0 | 3.0 |

Comparative Example 6: Preparation of Combination Bilayer Tablet Having Different Combination of Active Ingredients in the Discrete Part The procedure of Example 1 was repeated except for employing the ingredients as described in Table 5 below to obtain a combination bilayer tablet which comprises amlodipine and losartan in the first discrete part and rosuvastatin in the second discrete part.

TABLE 5

| Component | Ingredient (mg) | Comparative Example 6 |
|---|---|---|
| Discrete part comprising amlodipine + losartan | Amlodipine camsylate | 7.8 (Amlodipine, 5 mg) |
| | Losartan potassium | 100.0 (Losartan, 91.6 mg) |
| | Lactose hydrate | 52.0 |
| | Micro-crystalline cellulose | 104.0 |
| | Crospovidone | 10.0 |
| | Magnesium stearate | 2.0 |
| Discrete part comprising rosuvastatin | Rosuvastatin calcium | 20.8 (Rosuvastatin, 20 mg) |
| | Micro-crystalline cellulose | 182.0 |
| | Crospovidone | 15.0 |
| | Hydroxypropyl cellulose | 4.0 |
| | Magnesium stearate | 3.0 |

Comparative Example 7: Preparation of Combination Bilayer Tablet Having Different Combination of Active Ingredients in the Discrete Part The procedure of Example 1 was repeated except for employing the ingredients as described in Table 6 below to obtain a combination bilayer tablet which comprises amlodipine in the first discrete part and losartan and rosuvastatin in the second discrete part.

TABLE 6

| Component | Ingredient (mg) | Comparative Example 7 |
|---|---|---|
| Discrete part comprising amlodipine | Amlodipine camsylate | 7.8 (Amlodipine, 5 mg) |
| | Lactose hydrate | 52.0 |
| | Micro-crystalline cellulose | 104.0 |
| | Crospovidone | 10.0 |
| | Magnesium stearate | 2.0 |
| Discrete part comprising losartan + rosuvastatin | Losartan potassium | 100.0 (Losartan 91.6 mg) |
| | Rosuvastatin calcium | 20.8 (Rosuvastatin, 20 mg) |
| | Micro-crystalline cellulose | 182.0 |
| | Crospovidone | 15.0 |

TABLE 6-continued

| Component | Ingredient (mg) | Comparative Example 7 |
|---|---|---|
| | Hydroxypropyl cellulose | 4.0 |
| | Magnesium stearate | 3.0 |

Examples 4 to 6: Preparation of Combination Bilayer Tablet Having Different Amounts of Active Ingredients In accordance with the ingredients as described in Table 7 below, combination bilayer tablets which have different amounts of active ingredients than Examples 1 to 3 were prepared.

TABLE 7

| Component | Ingredient (mg) | Example 4 | Example 5 | Example 6 |
|---|---|---|---|---|
| Discrete part comprising amlodipine + rosuvastatin | Amlodipine camsylate | 7.8 (Amlodipine, 5 mg) | 7.8 | 7.8 |
| | Rosuvastatin calcium | 10.8 (Rosuvastatin, 10 mg) | 10.8 | 10.8 |
| | Lactose hydrate | 52.0 | 52.0 | 104.0 |
| | Micro-crystalline cellulose | 104.0 | 156.0 | 156.0 |
| | Crospovidone | 10.0 | 10.0 | 10.0 |
| | Magnesium stearate | 2.0 | 2.0 | 2.0 |
| | Ratio of lactose hydrate in the first layer | 28% | 22% | 36% |
| | Ratio of micro-crystalline cellulose in the first layer | 56% | 65% | 54% |
| Discrete part comprising losartan | Losartan potassium | 50.0 (Losartan, 45.8 mg) | 50.0 | 50.0 |
| | Micro-crystalline cellulose | 91.0 | 91.0 | 91.0 |
| | Crospovidone | 7.5 | 7.5 | 7.5 |
| | Hydroxypropyl cellulose | 2.0 | 2.0 | 2.0 |
| | Magnesium stearate | 1.5 | 1.5 | 1.5 |

Comparative Examples 8 to 10: Preparation of Combination Bilayer Tablet Having Different Amounts of Active Ingredients In accordance with the ingredients as described in Table 8 below, combination bilayer tablets were prepared by repeating the procedure of Example 1.

TABLE 8

| Component | Ingredient (mg) | Comparative Example 8 | Comparative Example 9 | Comparative Example 10 |
|---|---|---|---|---|
| Discrete part comprising amlodipine + rosuvastatin | Amlodipine camsylate | 7.8 (Amlodipine, 5 mg) | 7.8 | 7.8 |
| | Rosuvastatin calcium | 10.4 (Rosuvastatin, 10 mg) | 10.4 | 10.4 |
| | Lactose hydrate | — | 52.0 | 104.0 |
| | Micro-crystalline cellulose | 104.0 | 52.0 | 52.0 |
| | Crospovidone | 10.0 | 10.0 | 10.0 |
| | Magnesium stearate | 2.0 | 2.0 | 2.0 |
| | Ratio of lactose hydrate in the first layer | 0% | 39% | 56% |
| | Ratio of micro-crystalline cellulose in the first layer | 77% | 39% | 28% |
| Discrete part comprising losartan | Losartan potassium | 50.0 (Losartan, 45.8 mg) | 50.0 | 50.0 |
| | Micro-crystalline cellulose | 91.0 | 91.0 | 91.0 |
| | Crospovidone | 7.5 | 7.5 | 7.5 |
| | Hydroxypropyl cellulose | 2.0 | 2.0 | 2.0 |
| | Magnesium stearate | 1.5 | 1.5 | 1.5 |

Experimental Example 1: Dissolution Test of Single Layer Tablet and Bilayer Tablet Tablets prepared in Example 1 and Comparative Example 1 were each subjected to a drug dissolution test under the following conditions.

—Test Conditions—
Dissolution media: artificial gastric juice 900 mL (pH 1.2)
Apparatus: USP paddle method, 50 rpm
Temperature: 37° C.
Sampling: Dissolution media were taken 5, 10, 15, 30, 45, 60, 90 and 120 minutes after the test was commenced. The paddle speed was raised from 50 rpm to 150 rpm, and after 30 minutes, i.e., 150 minutes after the test was commenced, dissolution media was taken for final analysis.

—Analytical Conditions—
Column: stainless steel column (inner diameter: about 4.6 mm, length: 15 cm) packed with 3 μm of octadecylsilylated silica gel for liquid chromatography
Mobile phase: 6 mM sodium hexanesulfonate monohydrate/0.05% v/v phosphoric acid:acetonitrile (60:40, v/v)

(6 mM sodium hexanesulfonate monohydrate/0.05% v/v phosphoric acid:1.24 g of sodium 1-hexanesulfonate monohydrate was added to an 1 L flask, and 0.5 mL of phosphoric acid was carefully added. Distilled water was added and thoroughly stirred.)

Detector: ultraviolet spectrophotometer (absorbance at 254 nm)

Flow rate: 1.3 mL/min

Injection volume: 10 μL

Column temperature: 45° C.

—Test Criterion—

Dissolution rate of 80% or greater after 30 minutes (amlodipine, rosuvastatin)

Figure 2:
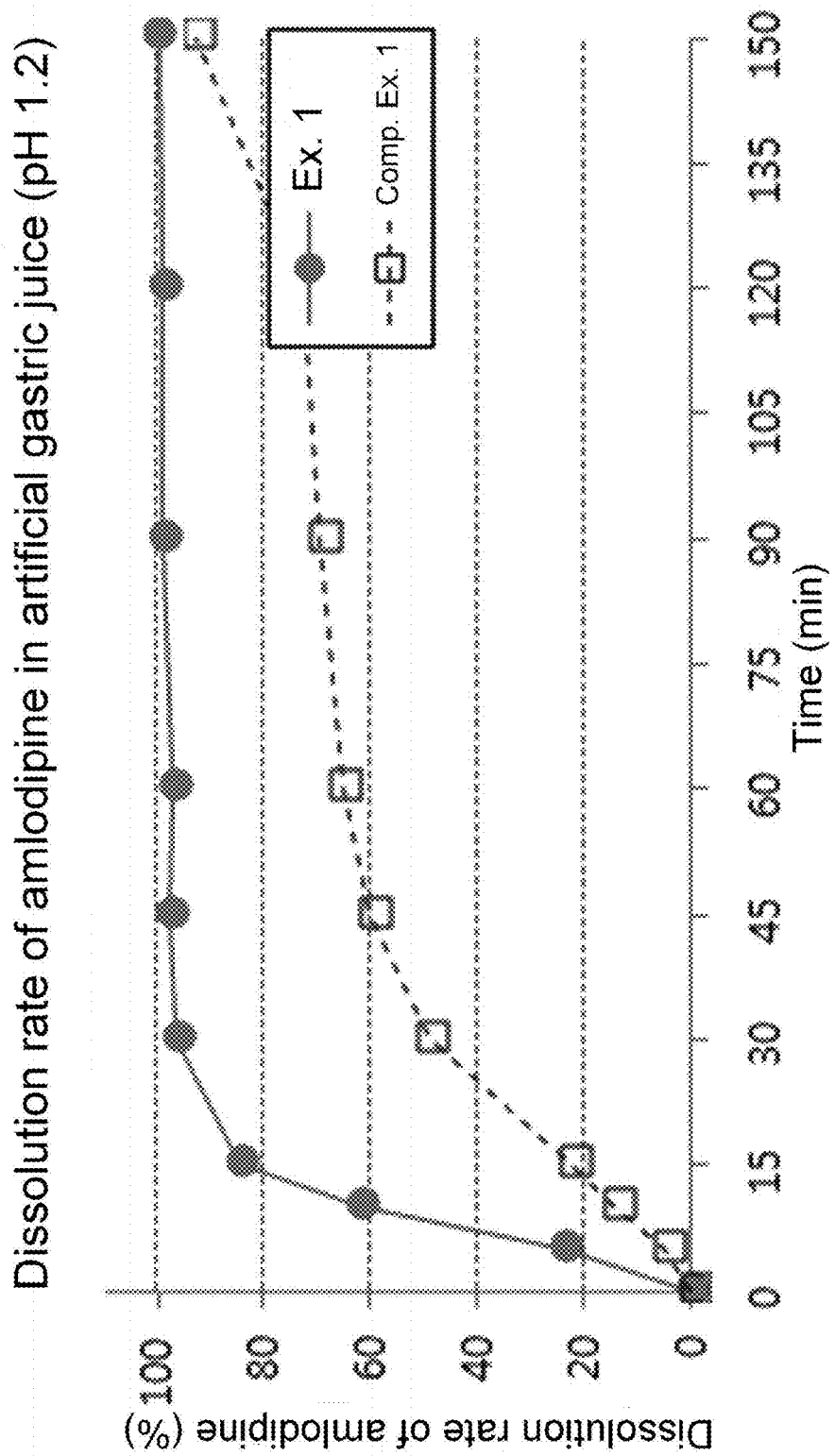
FIG. 2 is a graph showing dissolution rate of amlodipine in the formulations of Example 1 and Comparative Example 1.
Figure 3:
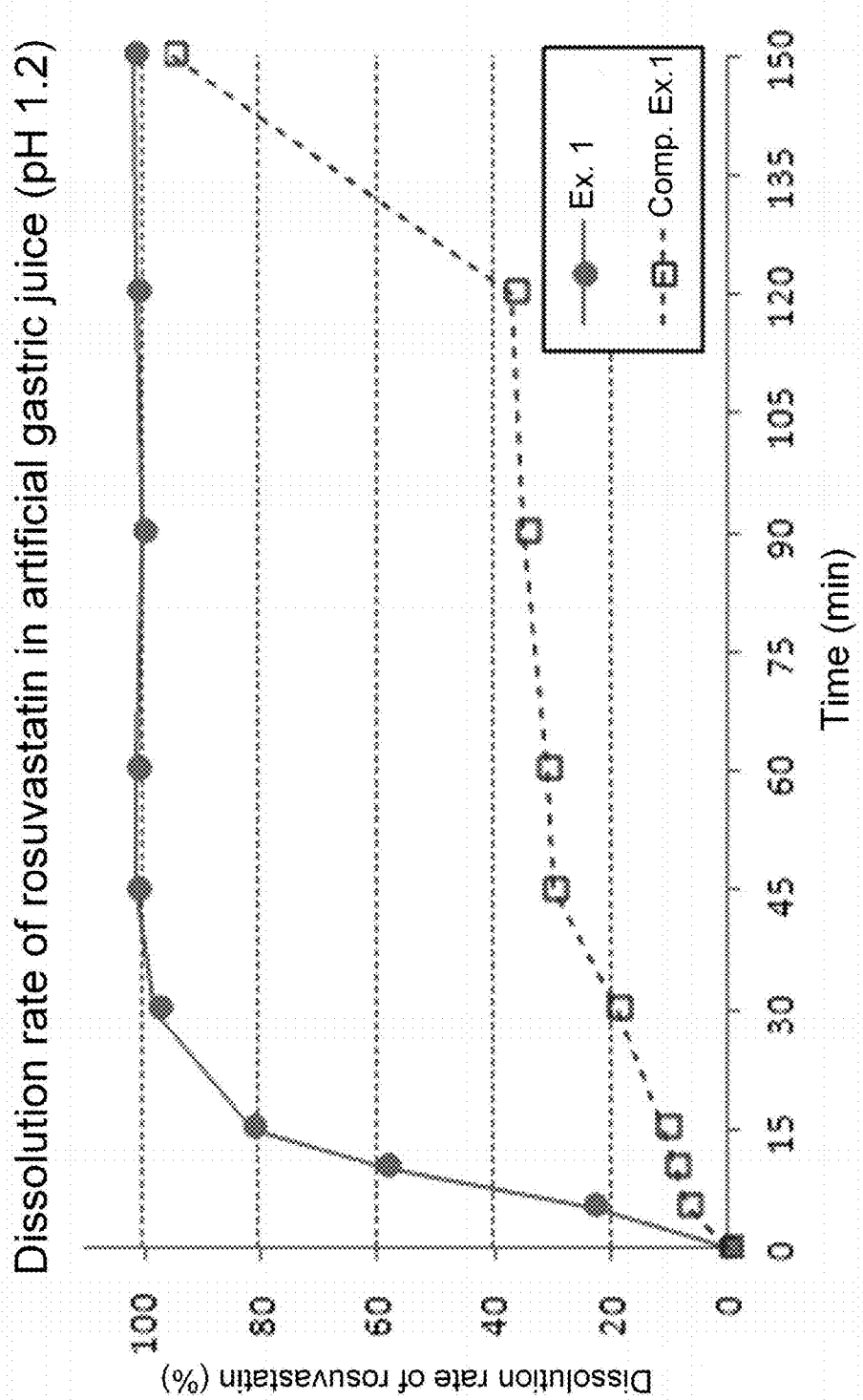
FIG. 3 is a graph showing dissolution rate of rosuvastatin in the formulations of Example 1 and Comparative Example 1.
Figure 4:
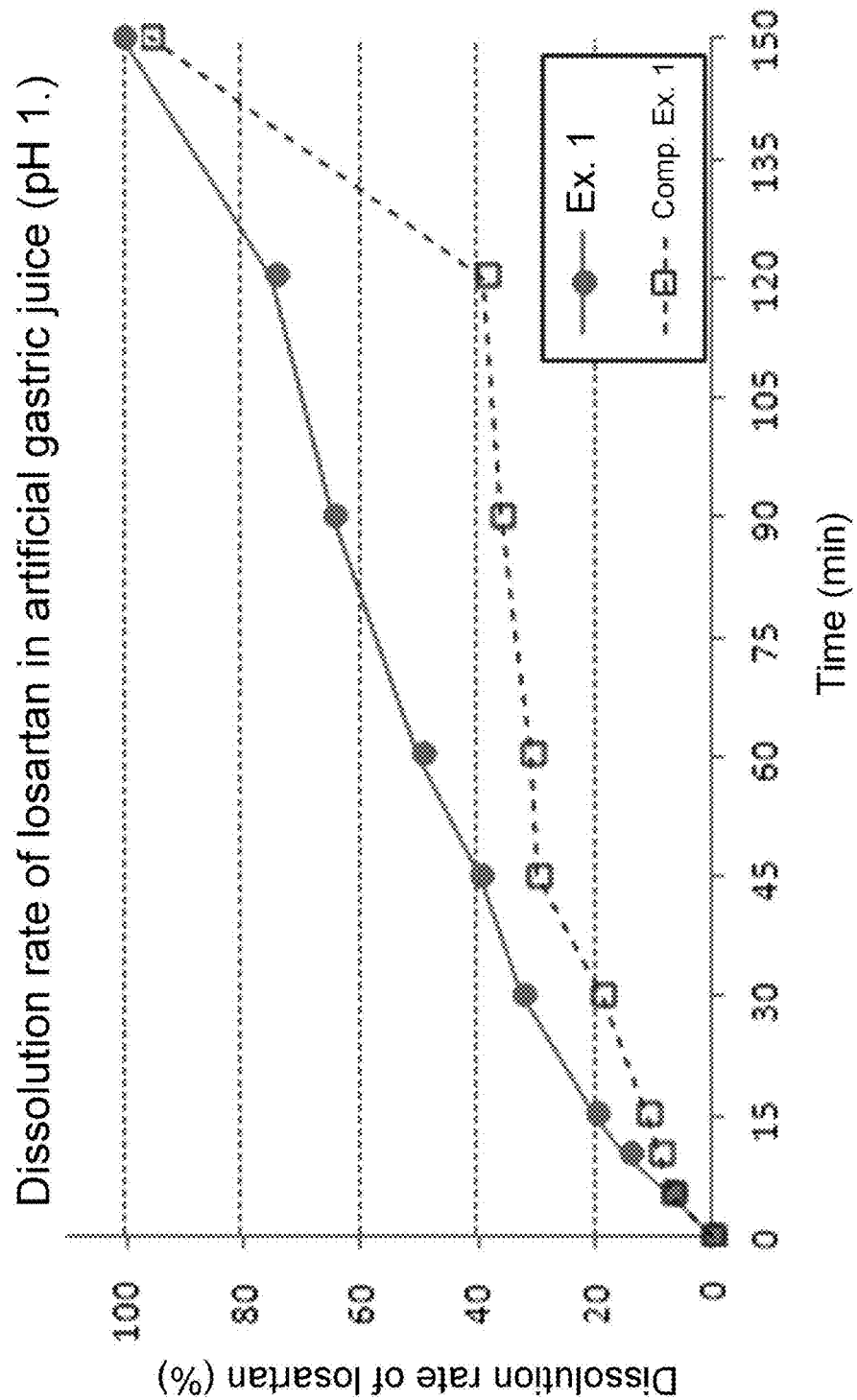
FIG. 4 is a graph showing dissolution rate of losartan in the formulations of Example 1 and Comparative Example 1.

The results of the dissolution test are shown in FIGS. 2 to 4. As shown in FIGS. 2 and 3, the bilayer tablet of Example 1 in which the discrete part comprising amlodipine and rosuvastatin and the discrete part comprising losartan are physically separated from each other exhibited a high dissolution rate as compared with the single layer tablet of Comparative Example 1 prepared by dry direct tableting. Also, unlike the single layer tablet of Comparative Example 1, the bilayer tablet of Example 1 showed a good dissolution profile of amlodipine and rosuvastatin, while satisfying the test criterion.

Moreover, as shown in FIG. 4, the bilayer tablet of Example 1 showed a significantly high dissolution rate of losartan compared with the single layer tablet of Comparative Example 1 which had dissolution rate of 40% or lower after 60 minutes.

The above results show that the gelation of losartan slows down the dissolution of amlodipine or rosuvastatin when losartan is present with amlodipine or rosuvastatin in the same layer.

Experimental Example 2: Dissolution Test of Bilayer Tablet with Compaction-Granulated Losartan Part and Bilayer Tablet Prepared by Dry Direct Tableting The bilayer tablet of Example 1 prepared by compaction granulation and the bilayer tablet of Comparative Example 2 prepared by simple mixing followed by dry direct tableting were each subjected to a dissolution test by using the same conditions as described in Experimental Example 1 on to evaluate dissolution rate of amlodipine, rosuvastatin and losartan. The results are shown in FIGS. 5 to 7.

Figure 7:
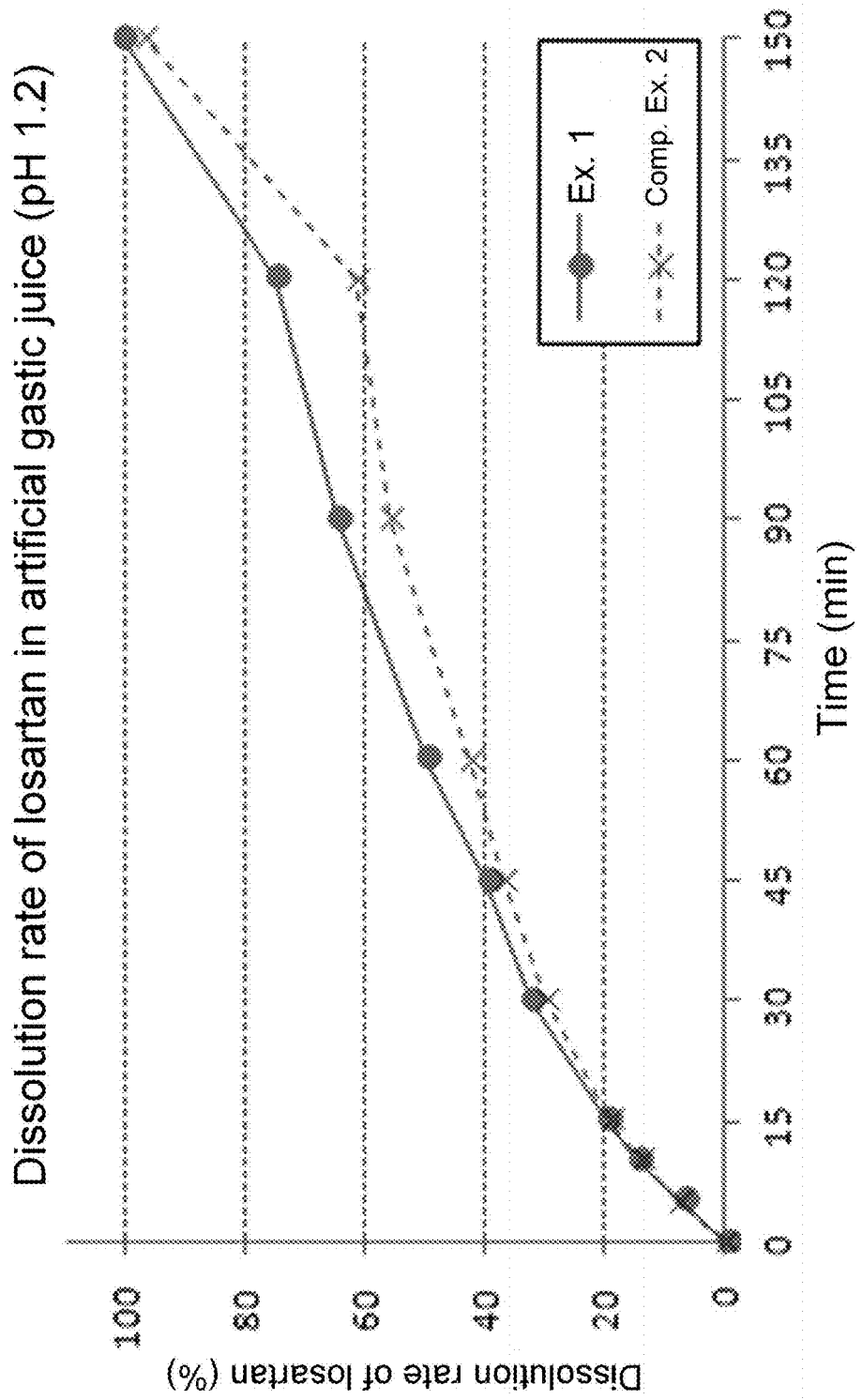
FIG. 7 is a graph showing dissolution rate of losartan in the formulations of Example 1 and Comparative Example 2.

As shown in FIG. 7, the bilayer tablet of Example 1 which was prepared by using a roller compactor and the bilayer tablet of Comparative Example 2 which was prepared without using a roller compactor did not show much difference in dissolution rate of losartan.

Figure 5:
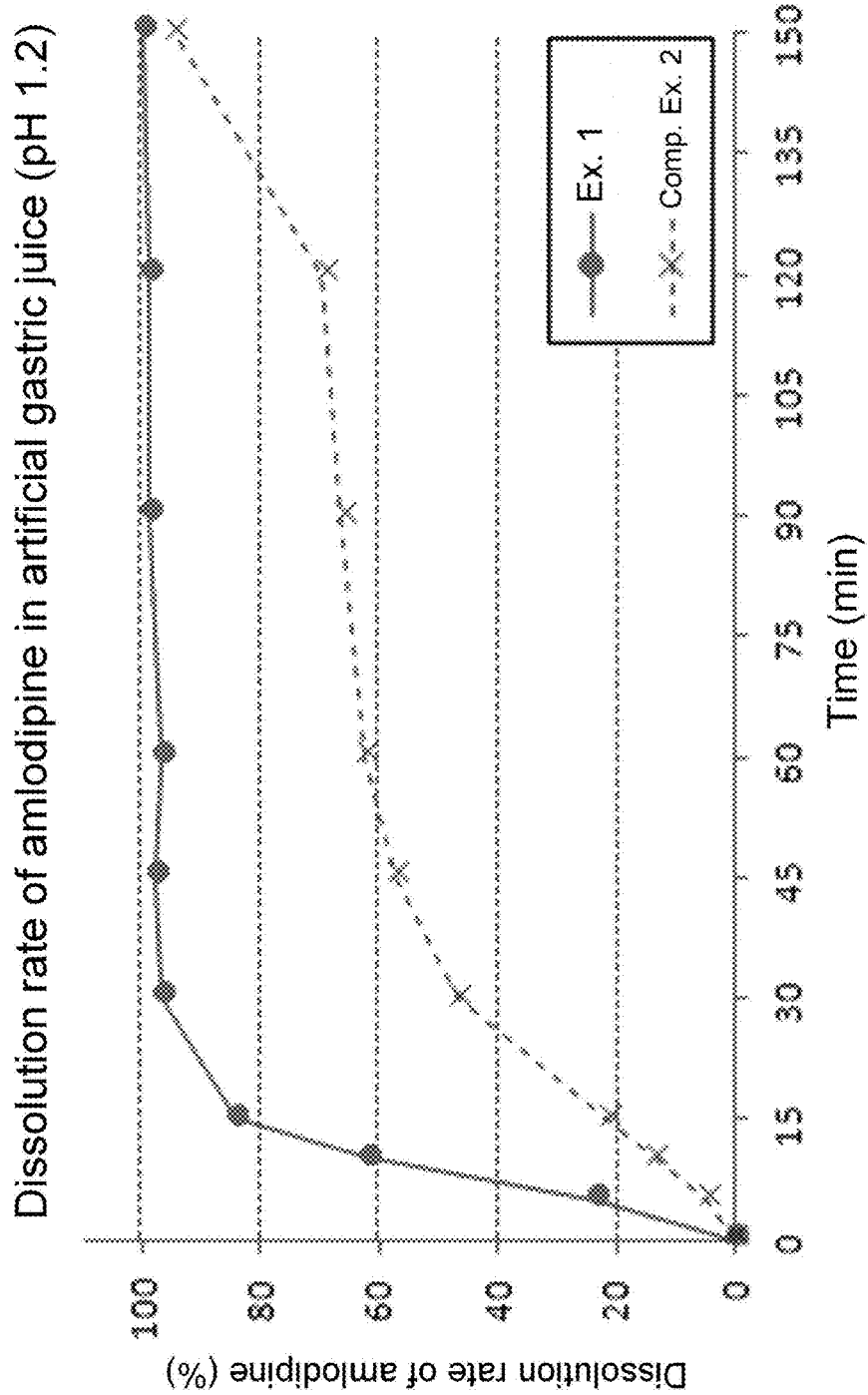
FIG. 5 is a graph showing dissolution rate of amlodipine in the formulations of Example 1 and Comparative Example 2.
Figure 6:
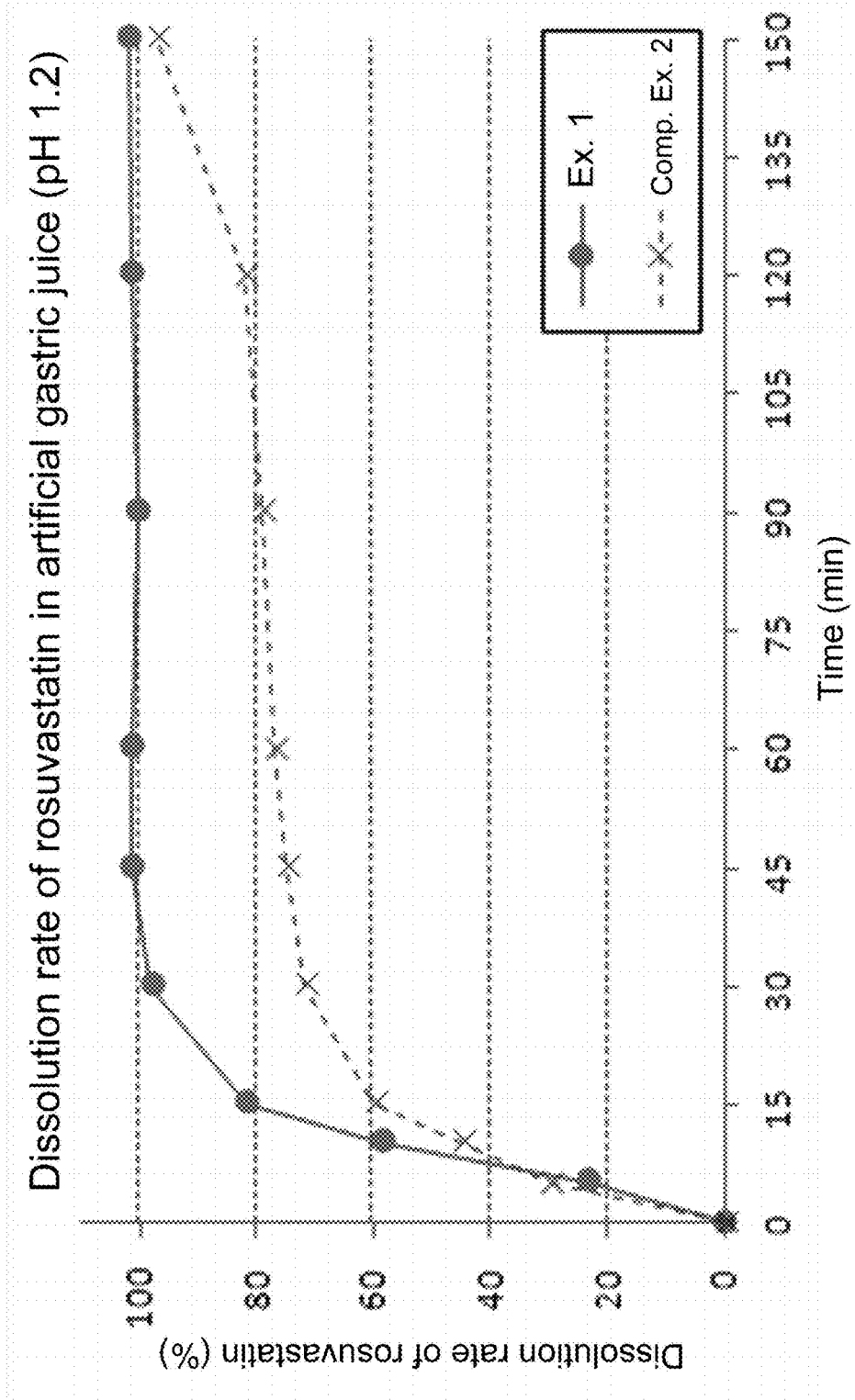
FIG. 6 is a graph showing dissolution rate of rosuvastatin in the formulations of Example 1 and Comparative Example 2.

However, as shown in FIGS. 5 and 6, the bilayer tablet of Comparative Example 2 which was prepared by simple mixing and dry direct tableting without using roller compactor exhibited a large deviation in dissolution, and a relatively low dissolution rate. Also, the bilayer tablet of Comparative Example 2 did not satisfy the test criterion (dissolution rate of 80% or greater after 30 minutes) in terms of amlodipine and rosuvastatin. Moreover, the losartan layer of Comparative Example 2 which was prepared without going through compaction granulation process, suffered from low productivity due to a problem associated with capping of the tablet. On the other hand, the bilayer tablet of Example 1 prepared by using a roller compactor showed an excellent dissolution rate of amlodipine and rosuvastatin, and also satisfied the test criterion.

The above results demonstrate that the roller compaction process of losartan granules not only affects dissolution profiles of three active ingredients, but also can affect the productivity of tableting process.

Experimental Example 3: Changes in Dissolution Rate Depending on the Ratio of Additives in Amlodipine-Rosuvastatin Layer A dissolution test was performed by using the same conditions as described in Experimental Example 1 on the bilayer tablets of Examples 1 to 3 and Comparative Examples 3 to 5 to evaluate dissolution rate of amlodipine, rosuvastatin and losartan. The results are shown in FIGS. 8 to 10.

Figure 10:
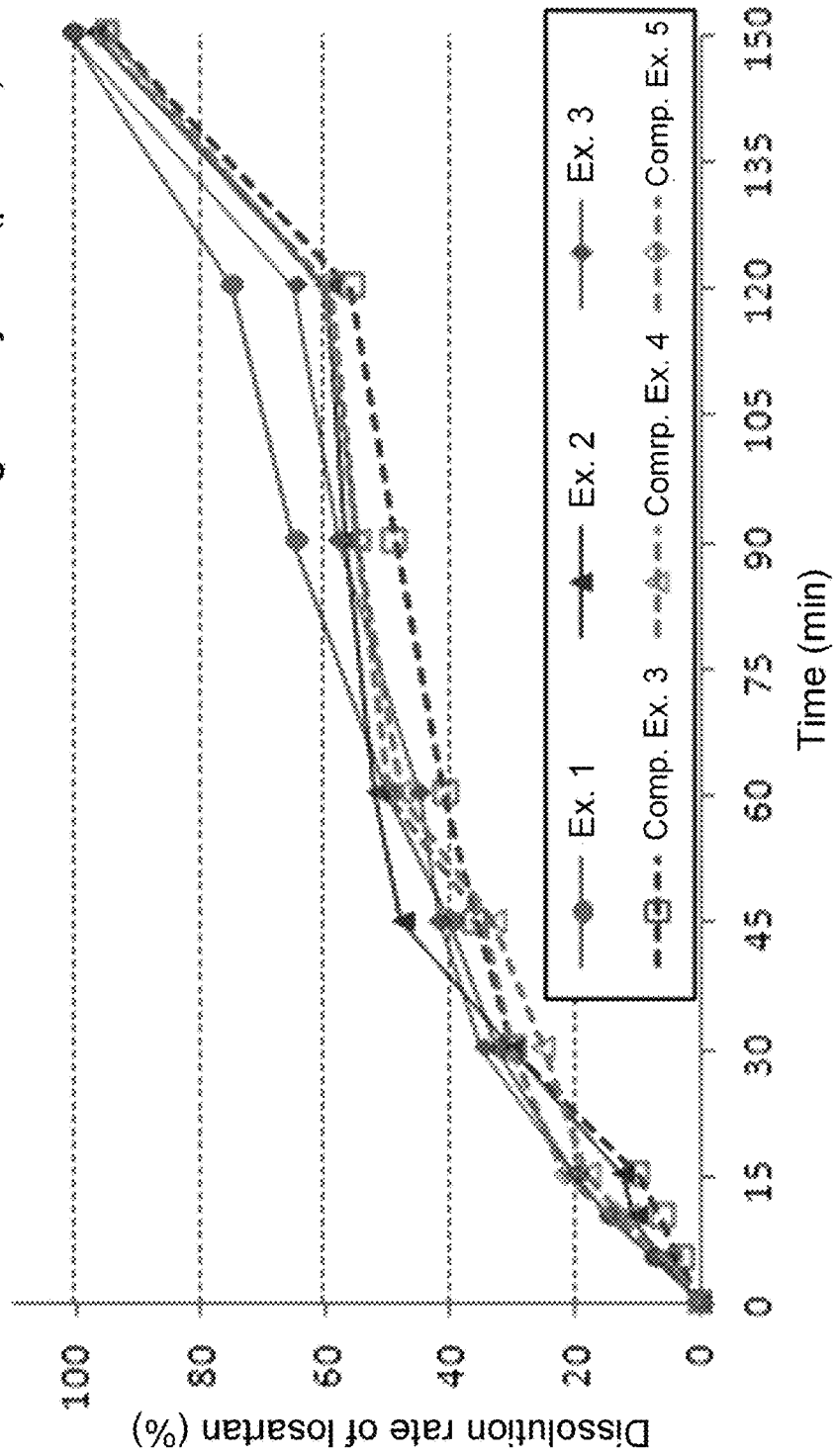
FIG. 10 is a graph showing dissolution rate of losartan in the formulations of Examples 1 to 3 and Comparative Examples 3 to 5.

As shown in FIG. 10, the bilayer tablets of Examples 1 to 3 and Comparative Examples 3 to 5 did not show much difference in dissolution rate of losartan.

Figure 8:
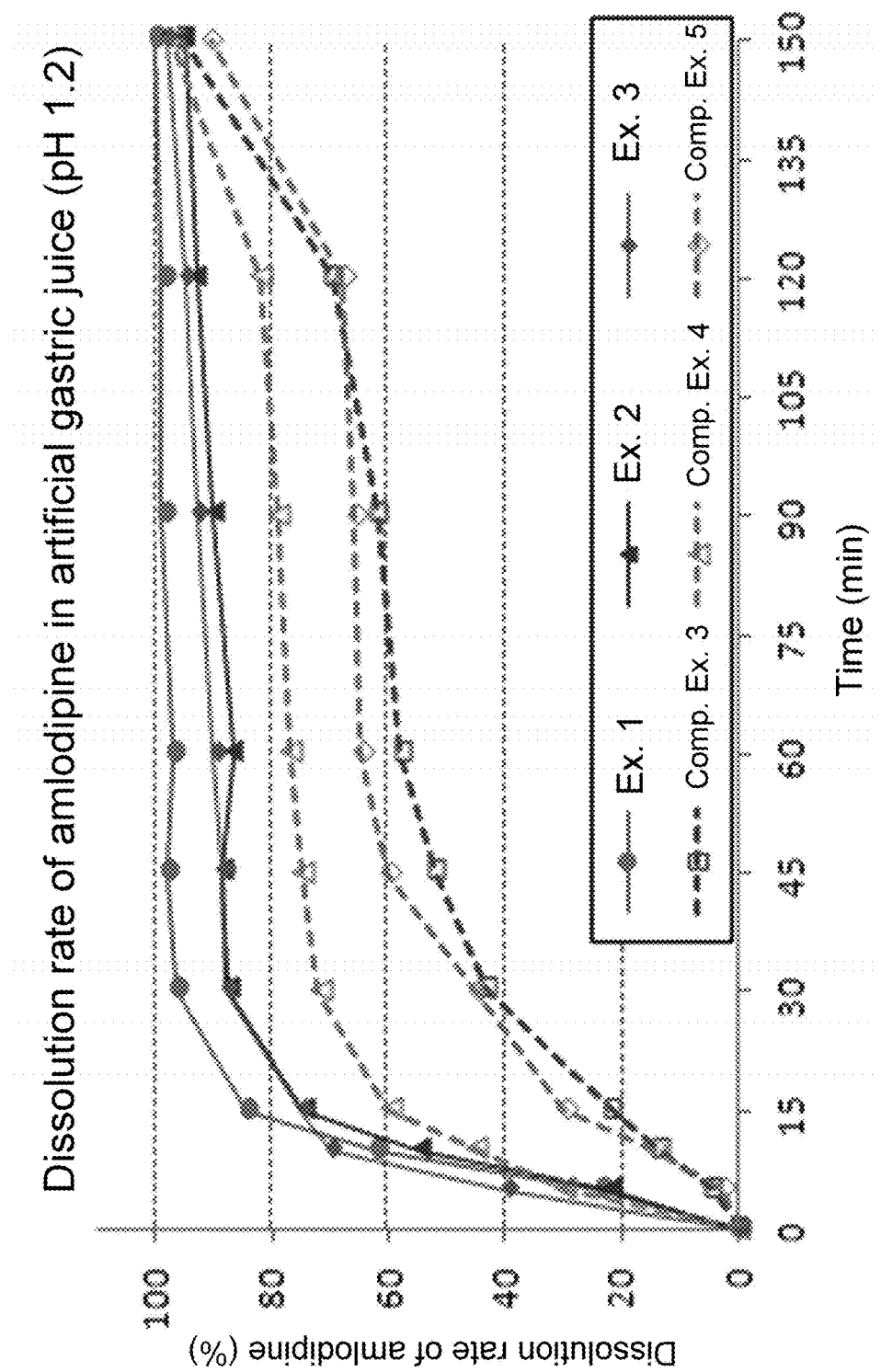
FIG. 8 is a graph showing dissolution rate of amlodipine in the formulations of Examples 1 to 3 and Comparative Examples 3 to 5.
Figure 9:
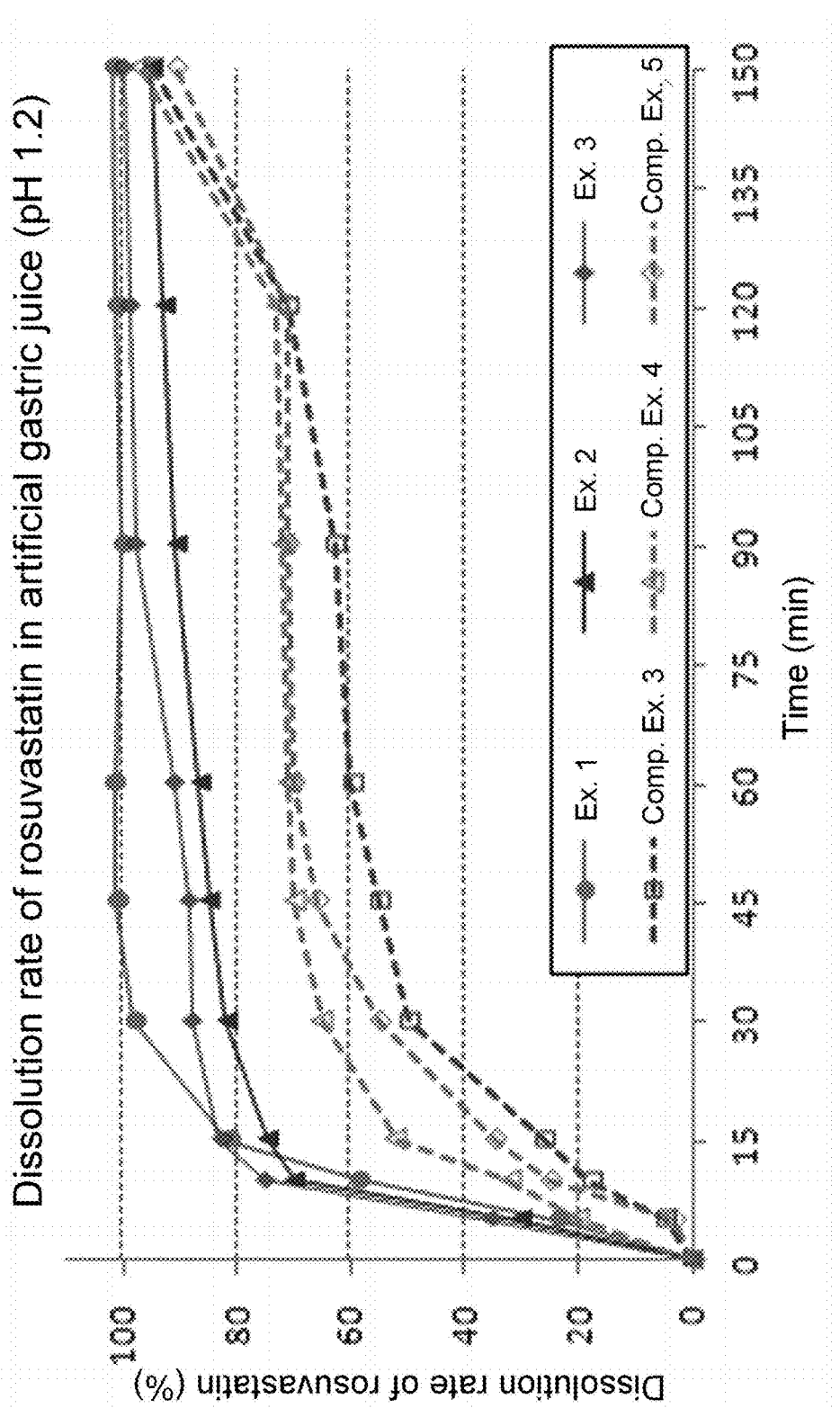
FIG. 9 is a graph showing dissolution rate of rosuvastatin in the formulations of Examples 1 to 3 and Comparative Examples 3 to 5.

However, as shown in FIGS. 8 and 9, the bilayer tablets of Examples 1 to 3 exhibited good dissolution profiles that satisfied the test criterion, whereas the bilayer tablets of Comparative Examples 3 to 5 failed to satisfy the test criterion.

The test results suggest that it is preferable, in terms of dissolution rate, to employ lactose hydrate and micro-crystalline cellulose in weight ratios of 20 to 40 wt % and 50 to 70 wt %, respectively, in the amlodipine-rosuvastain layer.

Experimental Example 4: Dissolution Test of Comparative Examples 6 (Tablet Comprising Amlodipine-Losartan Layer and Rosuvastatin Layer) and 7 (Tablet Comprising Amlodipine Layer and Losartan-Rosuvastatin Layer)

A dissolution test was performed by using the same conditions as described in Experimental Example 1 on the bilayer tablet of Example 1 and the bilayer tablets of Comparative Examples 6 and 7 to evaluate dissolution rate of amlodipine, rosuvastatin and losartan. The results are shown in FIGS. 11 to 13.

Figure 11:
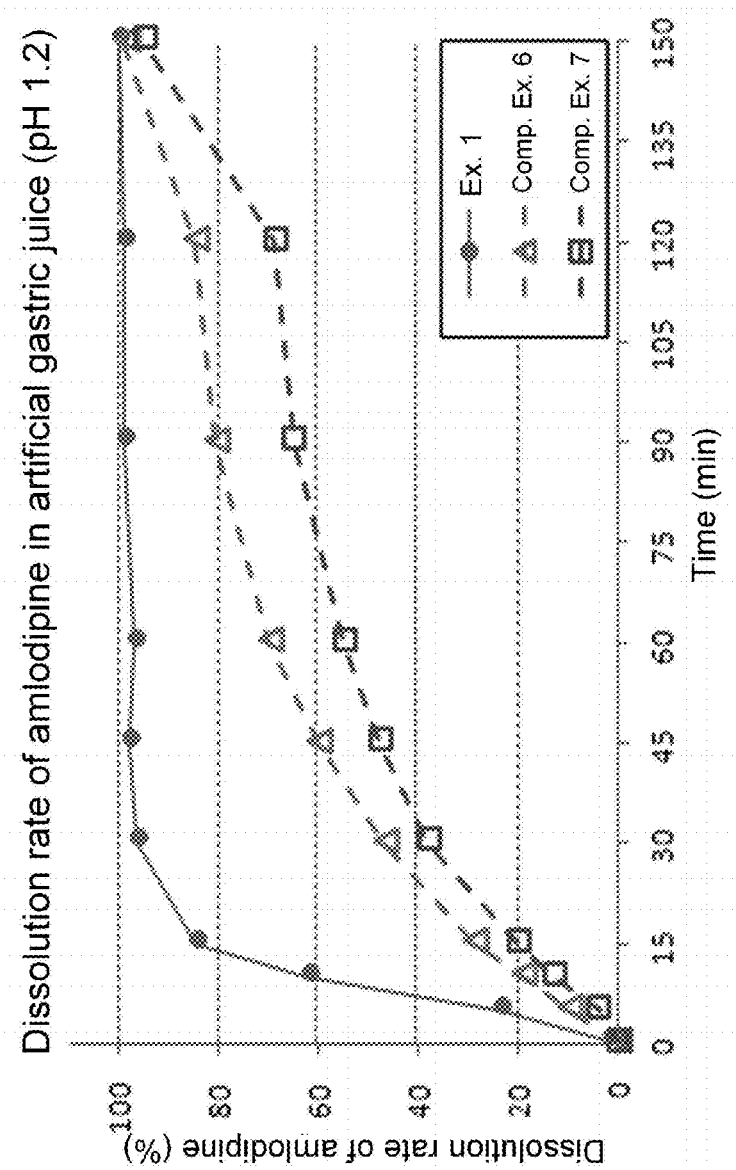
FIG. 11 is a graph showing dissolution rate of amlodipine in the formulations of Example 1 and Comparative Examples 6 and 7.
Figure 12:
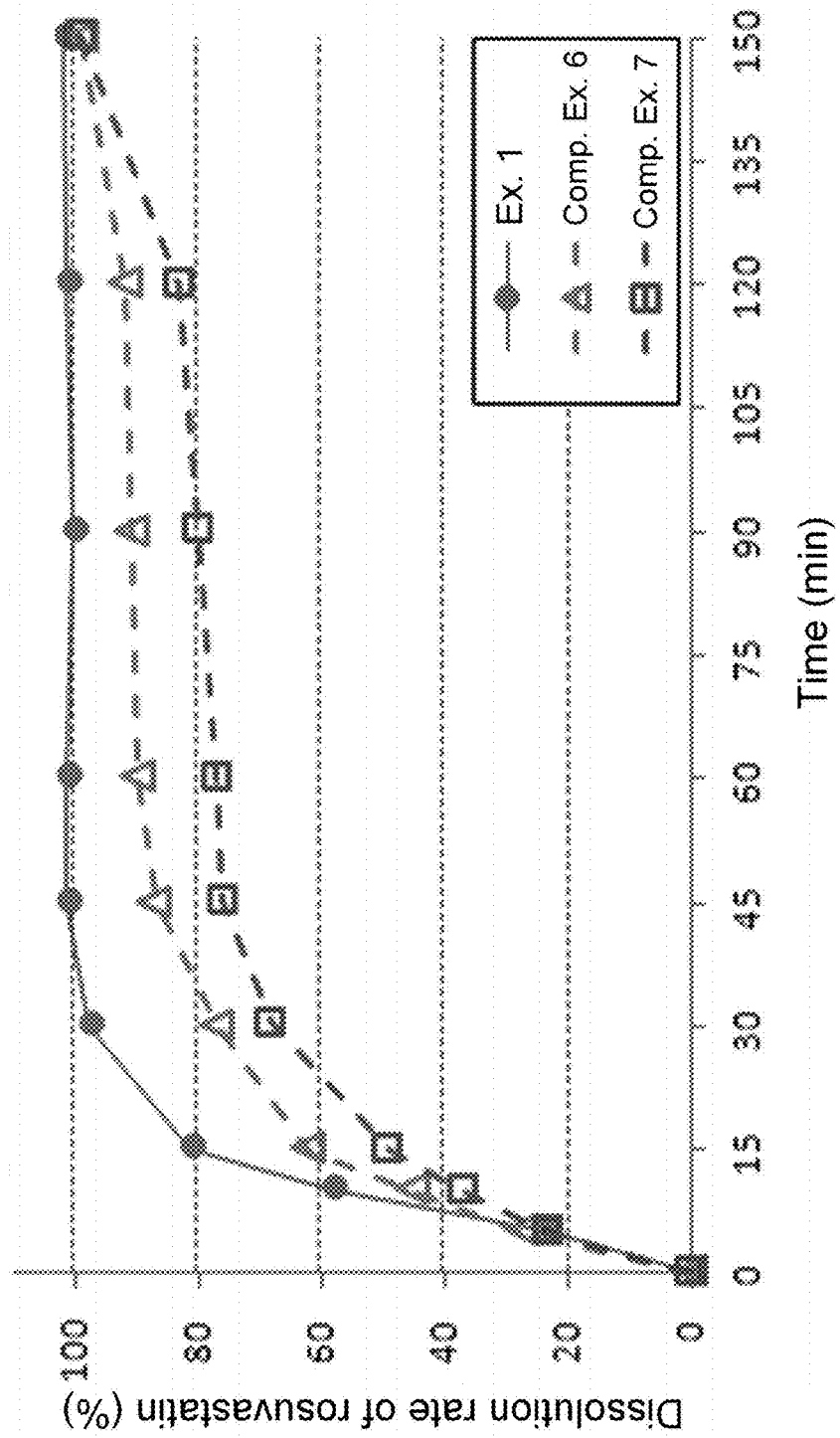
FIG. 12 is a graph showing dissolution rate of rosuvastatin in the formulations of Example 1 and Comparative Examples 6 and 7.
Figure 13:
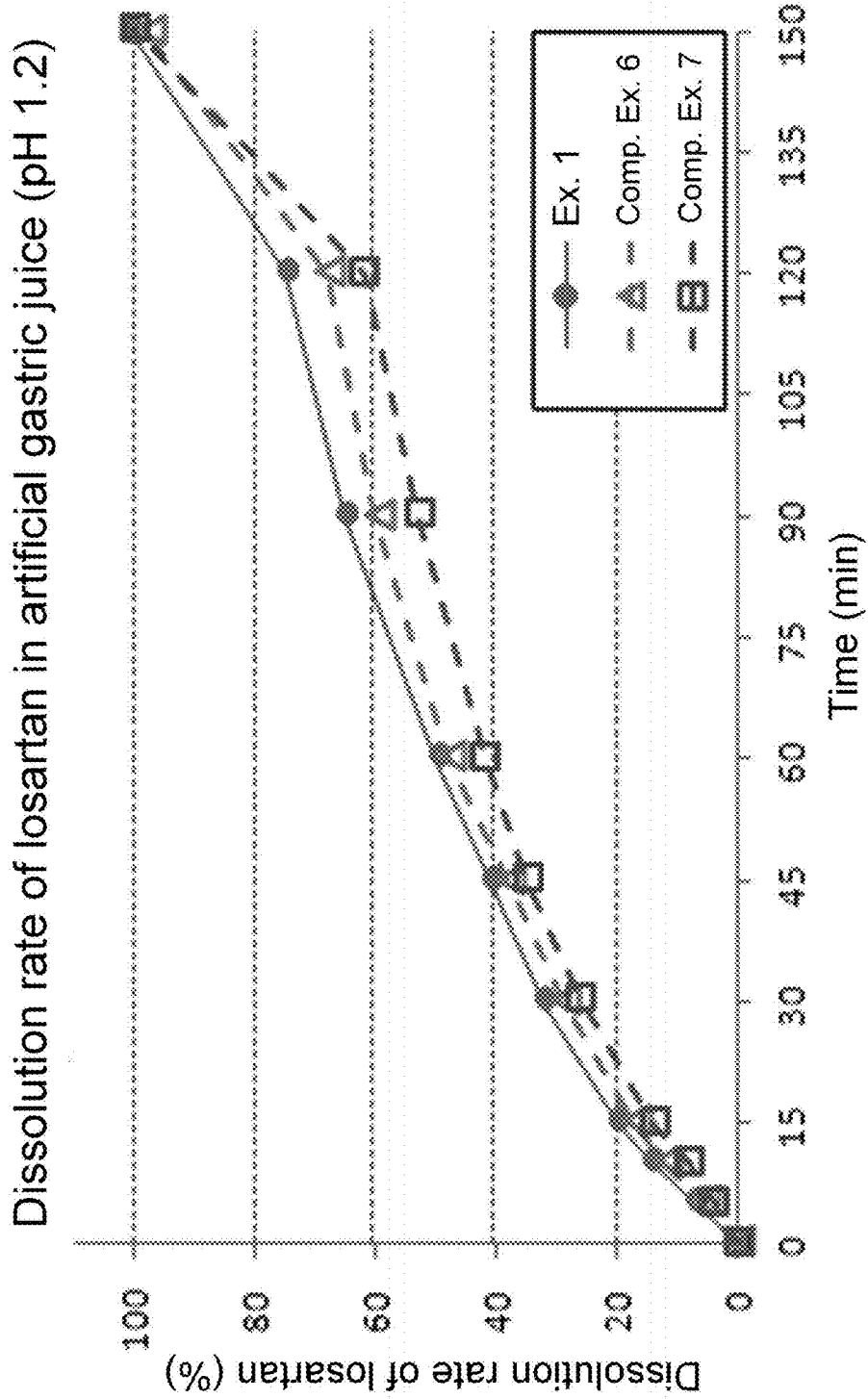
FIG. 13 is a graph showing dissolution rate of losartan in the formulations of Example 1 and Comparative Examples 6 and 7.

As shown in FIGS. 11 to 13, the bilayer tablet of Example 1 which comprises the amlodipine-rosuvastatin layer and the losartan layer exhibited a fast and high dissolution rate, and showed a good dissolution profile of amlodipine and rosuvastatin by meeting the test criterion. In contrast, the bilayer tablet of Comparative Example 6 having the amlodipine-losartan layer and the rosuvastatin layer and the bilayer tablet of Comparative Example 7 having the amlodipine layer and the losartan-rosuvastatin layer failed to pass the test criterion in terms of dissolution rate of all three ingredients.

The above results demonstrate that it is preferable to prepare a bilayer tablet comprising the amlodipine-rosuvastatin layer and the losartan layer, because a delay in dissolution is expected due to the gelation of losartan when a bilayer tablet comprises an amlodipine-losartan layer and a rosuvastatin layer or an amlodipine layer and a losartan-rosuvastatin layer. Thus, the results also show that a separation mode of said three drugs is critical in terms of dissolution rate.

Experimental Example 5: Stability Test Under Accelerated Storage Conditions

A stability test was performed for the tablets of Examples 1 to 3 under the following conditions to evaluate the stability of the tablets by analyzing the content change in amlodipine, rosuvastatin and losartan. The results are shown in Table 9.

—Accelerated Storage Test Condition—

Storage condition: stored in an HDPE bottle at 40° C., 75% RH

Test time: initial, 1, 2, 4 and 6 months

Analysis target: amlodipine, rosuvastatin and losartan

—Analytical Conditions—

Column: stainless steel column (inner diameter: about 4.6 mm, length: 15 cm) packed with 3 μm of octadecylsilylated silica gel for liquid chromatography Mobile phase: 6 mM sodium hexanesulfonate monohydrate/0.05% (v/v) phosphoric acid:acetonitrile (6:4, v/v)

Detector: ultraviolet spectrophotometer (absorbance at 254 nm)

Flow rate: 1.3 mL/min

Injection volume: 10 μL

Column temperature: 45° C.

TABLE 9

| Ingredient | Sample | Initial | 1 month | 2 months | 4 months | 6 months |
|---|---|---|---|---|---|---|
| Amlodipine | Example 1 | 100.0% | 99.7% | 99.5% | 99.2% | 99.1% |
| | Example 2 | 100.0% | 99.8% | 99.7% | 99.5% | 99.3% |
| | Example 3 | 100.0% | 99.8% | 99.5% | 99.3% | 99.1% |
| Rosuvastatin | Example 1 | 100.0% | 99.6% | 99.5% | 99.3% | 99.2% |
| | Example 2 | 100.0% | 99.5% | 99.4% | 99.3% | 99.1% |
| | Example 3 | 100.0% | 99.5% | 99.5% | 99.4% | 99.2% |
| Losartan | Example 1 | 100.0% | 99.8% | 99.7% | 99.3% | 99.1% |
| | Example 2 | 100.0% | 99.8% | 99.6% | 99.4% | 99.2% |
| | Example 3 | 100.0% | 99.7% | 99.5% | 99.3% | 99.1% | following conditions to analyze the changes in production rate of related substances of amlodipine, rosuvastatin and losartan under accelerated light and heat conditions. The results are shown in Table 10.

—Accelerated Test Conditions (Light Stability)—

(1) Apparatus: Xe-3-HC (Q-Lab)

(2) Temperature and humidity: 25° C.±2° C./60%±5% RH (3) Light: 0.80 W/m$^2$/nm, 18.44 hours (1,200,000 lux, method according to ICH Guidelines)

(4) Sample: stored on a Petri dish (5) Test time: initial and after the exposure —Accelerated Test Condition (Heat Stability)—

(1) Temperature and humidity: 50° C.±2° C.

(2) Sample: stored in an HDPE bottle (3) Test time: initial and after 28 days

—Analytical Conditions—

Column: stainless steel column (inner diameter: about 4.6 mm, length: 25 cm) packed with 5 μm of octadecylsilylated silica gel for liquid chromatography Mobile phase: 6 mM sodium hexanesulfonate monohydrate/0.05% (v/v) phosphoric acid:acetonitrile (6:4, v/v)

Detector: ultraviolet spectrophotometer (absorbance at 254 nm)

Flow rate: 1.0 mL/min

Injection volume: 10 μL

Column temperature: 45° C.

TABLE 10

| | Initial | | | Exposure to 1,200,000 lux | | | 50° C., stored in HDPE bottle After 28 days | | |
|---|---|---|---|---|---|---|---|---|---|
| Sample | Amlodipine related substance (%) | Rosuvastatin related substance (%) | Losartan related substance (%) | Amlodipine related substance (%) | Rosuvastatin related substance (%) | Losartan related substance (%) | Amlodipine related substance (%) | Rosuvastatin related substance (%) | Losartan related substance (%) |
| Ex. 1 | 0.02 | 0.01 | 0.01 | 0.13 | 0.10 | 0.04 | 0.08 | 0.10 | 0.04 |
| Ex. 2 | 0.01 | 0.02 | 0.02 | 0.14 | 0.15 | 0.05 | 0.06 | 0.15 | 0.04 |
| Ex. 3 | 0.03 | 0.01 | 0.01 | 0.11 | 0.11 | 0.05 | 0.13 | 0.11 | 0.05 |
| Comp. Ex. 1 | 0.10 | 0.05 | 0.03 | 1.29 | 1.75 | 0.09 | 1.05 | 0.75 | 0.55 |
| Comp. Ex. 2 | 0.03 | 0.03 | 0.02 | 0.20 | 0.28 | 0.06 | 0.10 | 0.16 | 0.05 |
| Comp. Ex. 3 | 0.02 | 0.01 | 0.01 | 0.14 | 0.21 | 0.04 | 0.12 | 0.14 | 0.04 |
| Comp. Ex. 4 | 0.02 | 0.02 | 0.01 | 0.12 | 0.17 | 0.05 | 0.08 | 0.12 | 0.04 |
| Comp. Ex. 5 | 0.01 | 0.02 | 0.01 | 0.10 | 0.17 | 0.04 | 0.11 | 0.17 | 0.05 |
| Comp. Ex. 6 | 0.09 | 0.02 | 0.04 | 1.10 | 0.19 | 0.10 | 0.97 | 0.13 | 0.34 |
| Comp. Ex. 7 | 0.01 | 0.06 | 0.04 | 0.15 | 0.30 | 0.08 | 0.10 | 0.72 | 0.20 |

As shown in Table 9 above, the bilayer tablets of Examples 1 to 3 exhibited insignificant changes in the content of amlodipine, rosuvastatin and losartan under 6 month accelerated storage, thereby indicating exceptionally good storage stability.

Experimental Example 6: Stability Test Under Accelerated Light and Heat Conditions A stability test was performed for the tablets prepared in Examples 1 to 3 and Comparative Examples 1 to 7 under the As shown in Table 10 above, the tablets of Examples 1 to 3 exhibited high stability under accelerated light and heat conditions, while producing a very small amount of amlodipine-, rosuvastatin- and losartan-related substances. On the other hand, the tablet obtained in Comparative Example 1, which was prepared by simple mixing of three ingredient followed by direct-compaction, produced related substances at least 5 to 10 times greater than the tablets obtained in Examples 1 to 3. This result indicates that tablets prepared by simple mixing have poor stability under accelerated light and heat conditions.

Additionally, the tablets obtained in Comparative Examples 6 and 7 produced related substances as much as Comparative Example 1. The test result of Comparative Example 6 shows that the bilayer tablet having the amlodipine-losartan layer and the rosuvastatin layer exhibits poor stability under accelerated light and heat conditions. Similarly, the test result of Comparative Example 7 shows that the bilayer tablet having the amlodipine layer and the losartan-rosuvastatin layer also exhibits poor stability under accelerated light and heat conditions.

This result indicates that the bilayer tablet having the amlodipine-rosuvastatin layer and the losartan layer of Examples 1 to 3 have significantly improved stability.

Experimental Example 7: Stability Test of Bilayer Tablets Having Different Amounts of Active Ingredient A stability test was performed for the tablets prepared in Examples 4 to 6 and Comparative Examples 8 to 10, which had different amounts of active ingredients, to evaluate dissolution rate of amlodipine, rosuvastatin and losartan. The results are shown in FIGS. 14 to 16.

Figure 14:
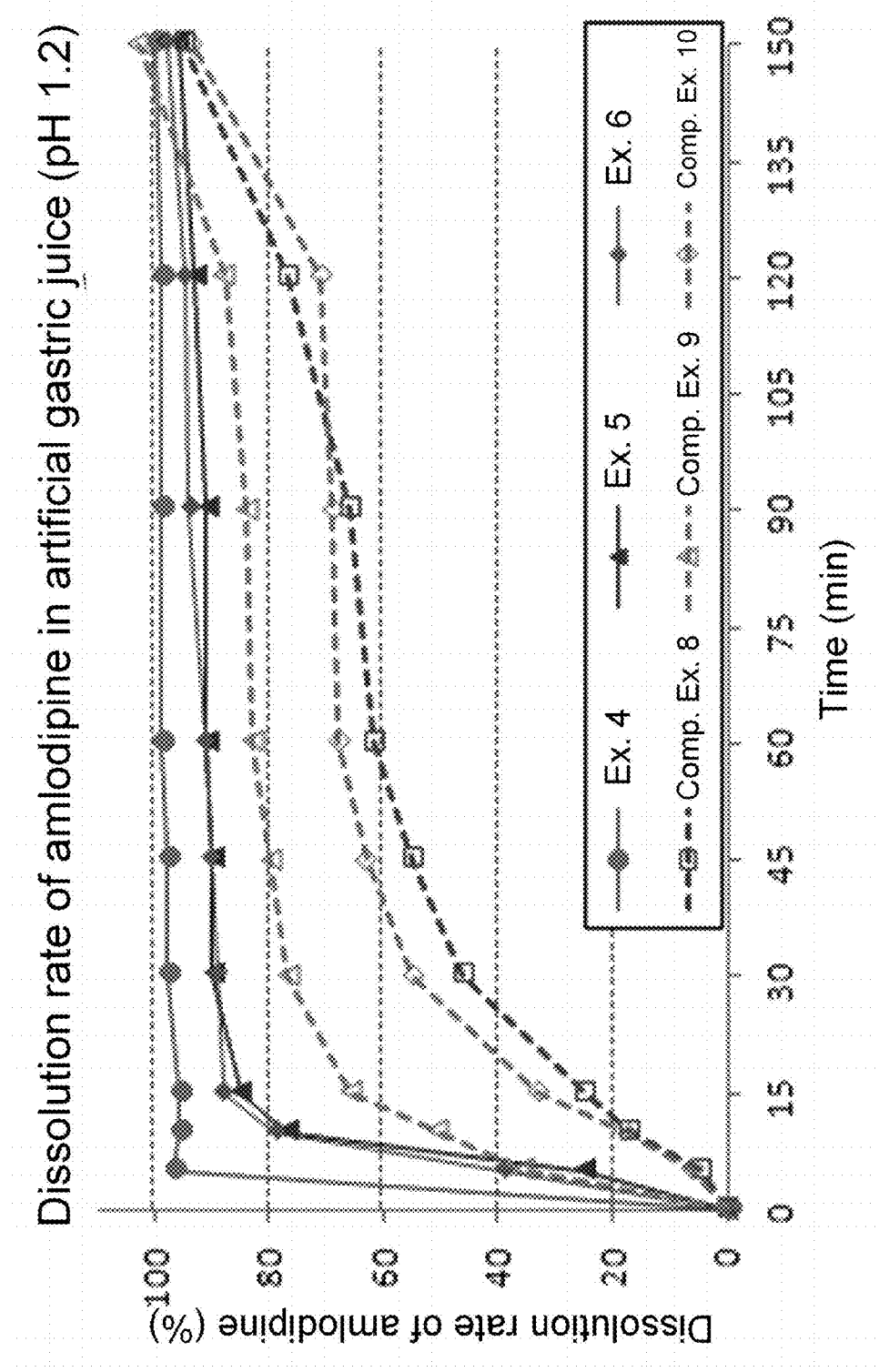
FIG. 14 is a graph showing dissolution rate of amlodipine in the formulations of Examples 4 to 6 and Comparative Examples 8 to 10.
Figure 15:
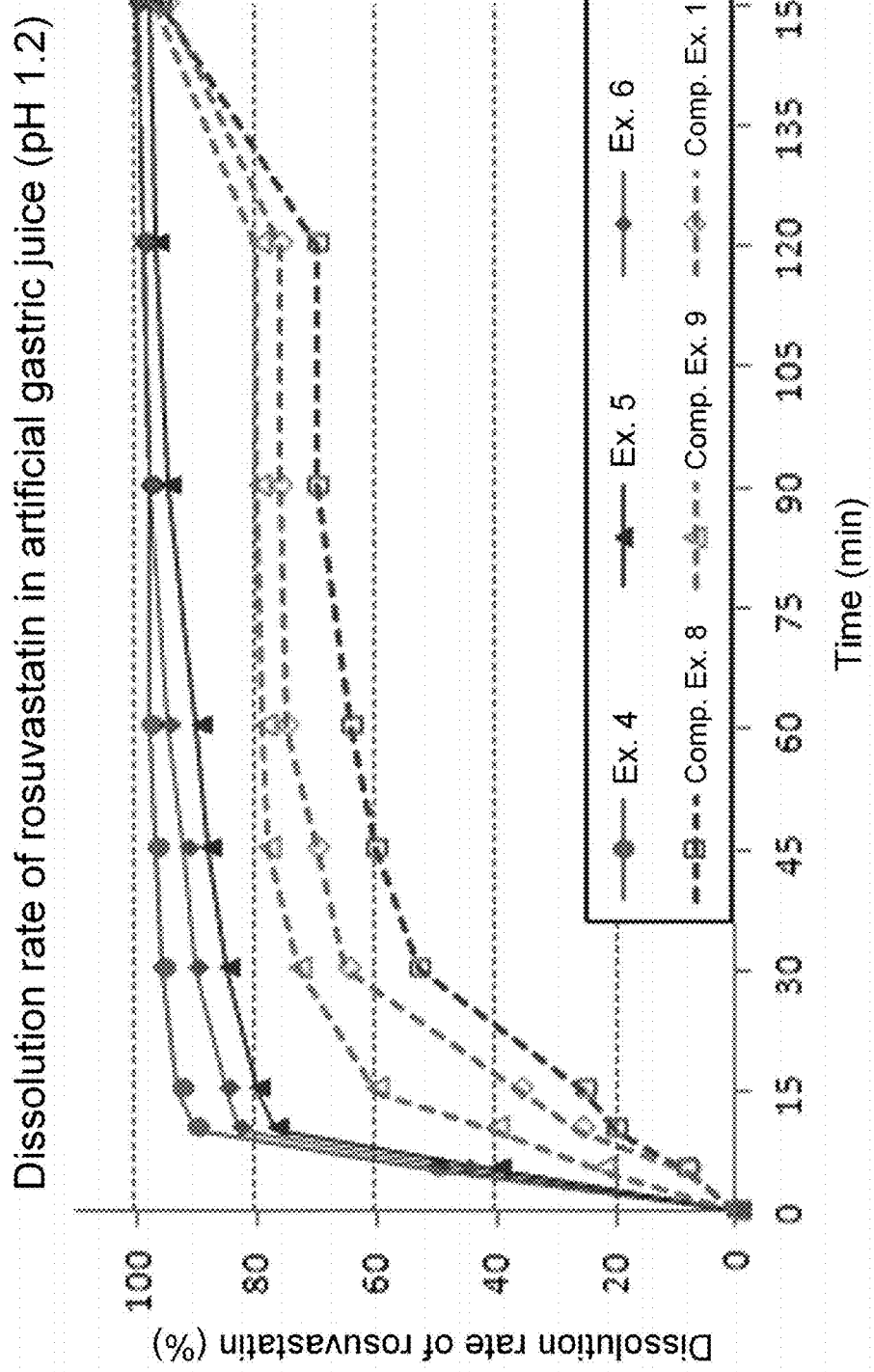
FIG. 15 is a graph showing dissolution rate of rosuvastatin in the formulations of Examples 4 to 6 and Comparative Examples 8 to 10.
Figure 16:
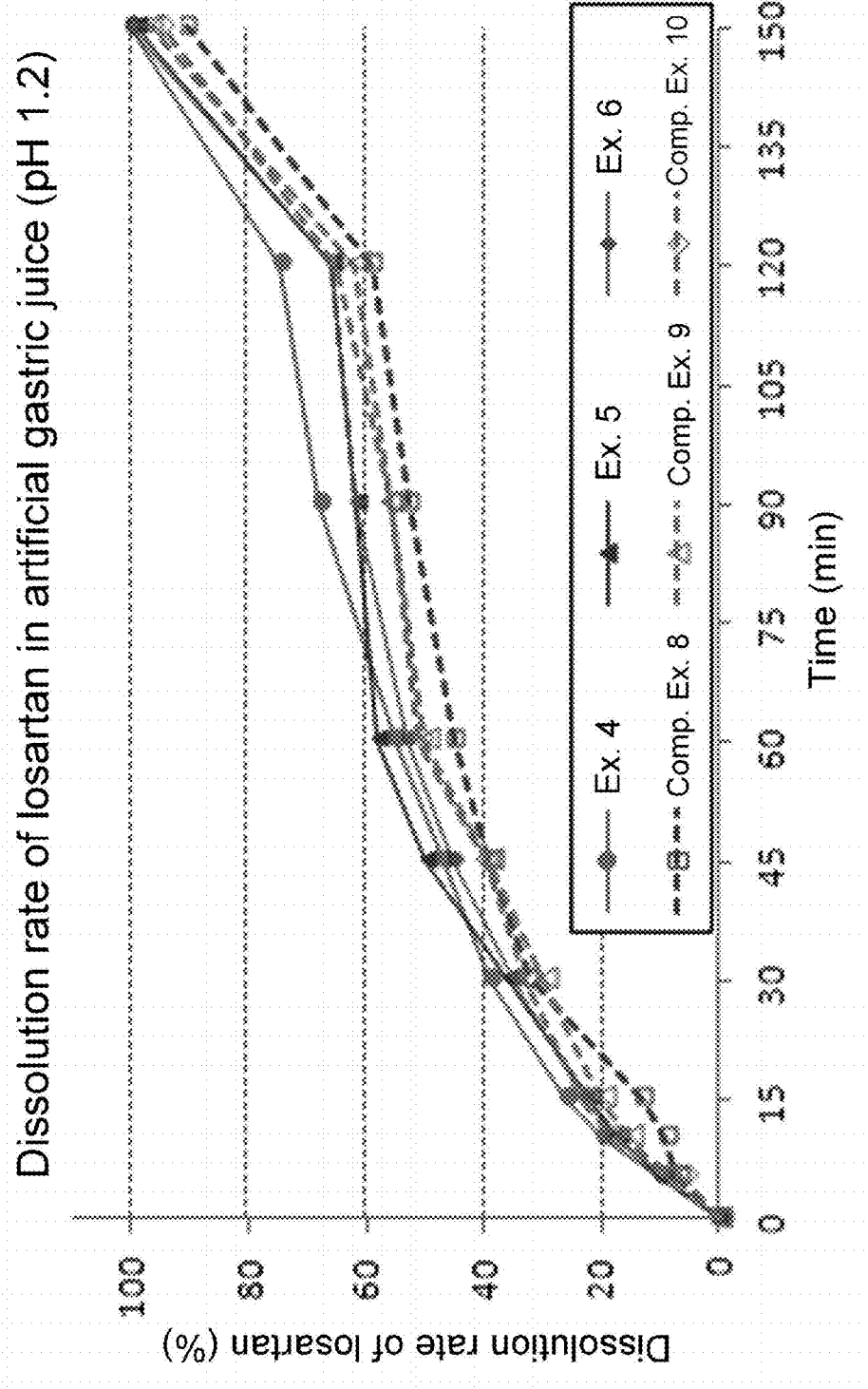
FIG. 16 is a graph showing dissolution rate of losartan in the formulations of Examples 4 to 6 and Comparative Examples 8 to 10.

As shown in FIGS. 14 to 16, the tablets of Examples 4 to 6, which contained 50 mg of losartan and 10 mg of rosuvastatin, exhibited similar dissolution profiles as those of Examples 1 to 3 and satisfied the test criterion.

On the other hand, the tablets of Comparative Examples 8 to 10 failed to pass the test criterion in terms of dissolution rates of amlodipine and rosuvastatin.

This result indicates that a tablet can maintain a good dissolution rate even if the amount of active ingredient changes, as long as the amlodipine-rosuvastatin layer contains the lactose hydrate in an amount of 20 to 40 wt %, and micro-crystalline cellulose in an amount of 50 to 70 wt %.

What is claimed is:

1. A pharmaceutical combination formulation, comprising:
   (1) a first discrete part comprising amlodipine or a pharmaceutically acceptable salt thereof, rosuvastatin or a pharmaceutically acceptable salt thereof and a pharmaceutically acceptable additive; and
   (2) a second discrete part comprising losartan or a pharmaceutically acceptable salt thereof and a pharmaceutically acceptable additive,
   wherein said discrete parts are physically separated from each other,
   wherein the first discrete part comprises lactose hydrate and micro-crystalline cellulose as the pharmaceutically acceptable additive, and
   wherein the lactose hydrate is included in an amount of 20 to 40 wt % based on the total weight of the first discrete part, and the micro-crystalline cellulose is included in an amount of 50 to 70 wt % based on the total weight of the first discrete part.

2. The pharmaceutical combination formulation of claim 1, wherein the combination formulation is in the form of a bilayer tablet comprising:
   (1) a first layer comprising amlodipine or a pharmaceutically acceptable salt thereof, rosuvastatin or a pharmaceutically acceptable salt thereof and a pharmaceutically acceptable additive; and
   (2) a second layer comprising losartan or a pharmaceutically acceptable salt thereof and a pharmaceutically acceptable additive.

3. The pharmaceutical combination formulation of claim 1, wherein the lactose hydrate and the micro-crystalline cellulose are included in a weight ratio of 1:1.5 to 1:3.

4. The pharmaceutical combination formulation of claim 1, wherein the second discrete part is in the form of granules prepared by a roller compaction process.

5. A fixed-dose combination formulation comprising:
   (1) a first discrete part comprising amlodipine or a pharmaceutically acceptable salt thereof, rosuvastatin or a pharmaceutically acceptable salt thereof and a pharmaceutically acceptable additive; and
   (2) a second discrete part comprising losartan or a pharmaceutically acceptable salt thereof and a pharmaceutically acceptable additive,
   wherein said discrete parts are physically separated from each other,
   wherein the first discrete part comprises lactose hydrate and micro-crystalline cellulose as the pharmaceutically acceptable additive, and
   wherein the lactose hydrate is included in an amount of 20 to 40 wt % based on the total weight of the first discrete part, and the micro-crystalline cellulose is included in an amount of 50 to 70 wt % based on the total weight of the first discrete part.

6. The fixed-dose combination formulation of claim 5, wherein the amount of amlodipine or a pharmaceutically acceptable salt thereof, as converted to amlodipine free base form, is 5 to 10 mg.

7. The fixed-dose combination formulation of claim 5, wherein the amount of rosuvastatin or a pharmaceutically acceptable salt thereof, as converted to rosuvastatin free acid form, is 10 to 20 mg.

8. The fixed-dose combination formulation of claim 5, wherein the amount of losartan or a pharmaceutically acceptable salt thereof, as converted to losartan free base form, is 45 to 100 mg.

9. A method for preparing a pharmaceutical combination formulation, which comprises the steps of:
   a) admixing amlodipine or a pharmaceutically acceptable salt thereof, rosuvastatin or a pharmaceutically acceptable salt thereof and a pharmaceutically acceptable additive to prepare a first discrete part;
   b) admixing losartan or a pharmaceutically acceptable salt thereof and a pharmaceutically acceptable additive to prepare a second discrete part; and
   c) loading the first discrete part prepared in step a) and the second discrete part prepared in step b) into a formulation, wherein said first and said second discrete parts are physically separated from each other,
   wherein the pharmaceutically acceptable additive in step a) comprises a lactose hydrate and micro-crystalline cellulose, and
   wherein the lactose hydrate is included in an amount of 20 to 40 wt % based on the total weight of the first discrete part, and the micro-crystalline cellulose is included in an amount of 50 to 70 wt % based on the total weight of the first discrete part.

10. The method for preparing a pharmaceutical combination formulation of claim 9, wherein step b) further comprises a granulizing step, and in step c) the discrete part obtained in step a) and the granules obtained in step b) are tableted to obtain a bilayer tablet.

* * * * *